United States Patent
Iadarola et al.

(10) Patent No.: US 6,596,269 B1
(45) Date of Patent: Jul. 22, 2003

(54) METHODS OF TREATING CHRONIC PAIN

(75) Inventors: Michael J. Iadarola, Washington, DC (US); Robert M. Caudle, Gainesville, FL (US); Alan A. Finegold, Bethesda, MD (US); Andrew J. Mannes, Chevy Chase, MD (US); Zoltan Olah, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/787,660

(22) PCT Filed: Sep. 23, 1999

(86) PCT No.: PCT/US99/22103

§ 371 (c)(1),
(2), (4) Date: Aug. 24, 2001

(87) PCT Pub. No.: WO00/16800

PCT Pub. Date: Mar. 30, 2000

Related U.S. Application Data

(60) Provisional application No. 60/100,901, filed on Sep. 23, 1998.

(51) Int. Cl.[7] .................. A61K 48/00; C12N 15/86; C12N 15/861; C12N 15/864
(52) U.S. Cl. ............. 424/93.2; 424/199.1; 435/320.1; 435/235.1
(58) Field of Search ............. 424/93.2, 199.1; 435/235.1, 320.1

(56) References Cited

U.S. PATENT DOCUMENTS

| | | |
|---|---|---|
| 4,313,937 A | 2/1982 | Oyama |
| 4,350,764 A | 9/1982 | Baxter et al. |

FOREIGN PATENT DOCUMENTS

| | | |
|---|---|---|
| EP | 0 035 781 A2 | 9/1981 |
| WO | 96/40959 | 12/1996 |
| WO | 97/00947 | 1/1997 |
| WO | 98/38326 | 9/1998 |

OTHER PUBLICATIONS

Mannes et al (Brain Research 793:1–6, 1998).*
Wu et al (Journal of Neuroscience 14(8):4806–14, 1994).*
Almay et al., "Endorphins in chronic pain. I. Differences in CSF endorphin levels between organic and psychogenic pain syndromes," *Pain* (1978) 5: 153–162.
Beutler et al., "Retrovirus–mediated expression of an artificial beta–endorphin precursor in primary fibroblasts," *Journal of Neurochemistry* (1995) 64: 475–81.
Calvino et al., Chronic pain induces a paradoxical increase in growth hormone secretion without affecting other hormones related to acute stress in the rat, *Pain* (1992) 49: 27–32.
Finegold et al., "A paracrine paradigm for in vivo gene therapy in the central nervous system: treatment of chronic pain," *Human Gene Therapy* (May 1999) 10(7): 1251–7.
Fujita et al.., "Gene targeting with a replication–defective adenovirus vector," *Journal of Virology* (Oct. 1995) 69(10): 6180–6190.
Kamei et al., "Effect of diabetes on the antinociceptive effect of beta–endorphin," *Brain Research* (1993) 619: 76–80.
Kremer and Perricaudet, "Adenovirus and adeno–associated virus mediated gene transfer," *British Medical Bulletin* (1995) 51(1): 31–44.
Lipman et al., "Peak B endorphin concentration in cerebrospinal fluid: reduced in chronic pain patients and increased during the placebo response," *Psychopharmacology* (1990) 102: 112–116.
Mannes et al., "Beta–endorphin expression by a replication-–defective adenovirus," *Regional Anesthesia and Pain Medicine* (May 1999) 24(3), Abstract XP000867377.
Mannes et al., "Adenoviral expression of beta–endorphin in cell cultures," *Anesthesiology* (Sep. 1998) 89(3a), Abstract XP000867363.
Przewlocki, "Opioid peptides in relation to antinociception," *Pol. J. Pharmacol. Pharm.* (1987) 39: 609–621.
Saitoh et al. "Dose–dependent doxycycline–mediated adrenocorticotropic hormone secretion from encapsulated Tet–on proopiomelanocortin Neuro2A cells in the subarachnoid space," *Human Gene Therapy* (May 1998) 9(7): 997–1002, Abstract XP000867278.
Smith, "Adenovirus–mediated gene transfer to treat neurologic disease," *Arch Neurol.* (Aug. 1998) 55: 1061–1064.
Tanelian et al., "Gene therapy with adenoviral beta–endorphin is antinociceptive," *Anesthesiology* (Sep. 1996) 86(3a): Abstract XP000867358.
Tseng et al., "Spinal δ2 but not δ1 opioid receptors are involved in intracerebroventricular β–endorphin–induced antinociception in the mouse," *Life Sciences* (1993) 52: PL 211–215.
Young et al., Release of β–endorphin and methionine–enkephalin into cerebrospinal fluid during deep brain stimulation for chronic pain, *J. Neurosurg.* (1993) 79: 816–825.

* cited by examiner

*Primary Examiner*—Mary E. Mosher
(74) *Attorney, Agent, or Firm*—Townsend and Townsend and Crew LLP

(57) ABSTRACT

This invention pertains to the surprising discovery of novel compositions and methods which selectively treat chronic pain while not significantly affecting basal nociceptive, acute pain, responses. The invention provides for compositions and methods of treating chronic pain by administering beta-endorphin-expressing recombinant expression systems such as adenovirus or adeno-associated virus into a sub-arachnoid or epidural space. The recombinant virus infects the pia mater connectve tissue cells and the infected cells express the fusion protein, wherein the fusion protein is secreted into the spinal cord parenchymal tissue in an amount effective to treat the chronic pain but not significantly affecting basal nociceptive responses.

20 Claims, 2 Drawing Sheets

METHODS OF TREATING CHRONIC PAIN

CROSS REFERENCE TO RELATED APPLICATIONS

This application is a US national phase application of PCT/US99/22103, filed Sep. 23, 1999, which claims the benefit of U.S. provisional application No. 60/100,901, filed Sep. 23, 1998.

FIELD OF THE INVENTION

This invention generally pertains to the field of medicine and pain control. In particular, this invention pertains to the surprising discovery that pia mater cells transformed to secrete beta-endorphin will selectively control chronic pain while not significantly affecting basal nociceptive, acute pain, responses.

BACKGROUND OF THE INVENTION

This invention is the surprising discovery of a method of using beta endorphin through genetic engineering to treat chronic pain, while at the same time not significantly affecting the ability to react to acutely painful, potentially dangerous, stimuli. As will be explained below, prior to this invention, there was a great amount of academic debate as to whether beta-endorphin can be used to treat or control chronic pain. Thus, the discovery of beta-endorphin's selective control of chronic pain when secreted by transformed pia mater cells was unpredictable and therapeutically advantageous.

Current analgesic therapies often fall short of therapeutic goals and typically have unacceptable side effects. In many chronic pain syndromes, such as those subsequent to neuropathic injury, pain is not well controlled by any currently available method. Furthermore, most chronic pain treatment regimes affect the patient's ability to perceive acute pain, thus blunting or abrogating necessary protective basal nociceptive responses.

Exogenous opioids, such as morphine, are commonly used to treat chronic pain. Unfortunately, such drugs are addictive and result in side effects, such as nausea and constipation. Such side effects can be reduced by delivery into the subarachnoid space through intrathecal pumps. However, pumps are expensive and invasive, leading to possible risk of infection. Tolerance and dependence to exogenous opioids is also a severe medical and public health problem.

Endogenous opioids as analgesics for the treatment of acute and chronic pain has also been the subject of many studies. There are numerous endogenous opioids, including, e.g., the beta-endorphin peptide family, enkephalins, dynorphins (see, e.g., Cesselin (1995) Fundam. Clin. Pharmacol. 9:409–433). In particular, investigators have focused on the role and use of beta-endorphins as mediators of the body's response to pain.

However, studies have generated conflicting theories as to the role beta-endorphin plays in both acute and chronic pain. Thus, to date, the specific role of beta-endorphin in the physiology and neurotransduction of pain has not been determined.

The vast majority of studies implicate beta-endorphin as an endogenous mediator of acute pain and stress. For example, Dionne (1998) Clin. Pharmacol. Ther. 63:694–701, reported that administration of the analgesic ibuprofen suppresses both acute pain and the plasma beta-endorphin levels seen after oral surgery (tooth extraction). In Kamei (1993) Brain Res. 13:619:76–80, intrathecal administration of beta-endorphin had clear anti-nociceptive effects when acute pain was induced (by heat) in rats (tail-flick response). Tseng (1993) Life Sci. 52:PL211–215; also concluded that beta-endorphin induced anti-nociception in a mouse acute pain (tail-flick response) model. Przewlocki (1987) Pol. J. Pharmacol. Pharm. 39:609–621, reported an enhanced release of beta-endorphin in the brain and pituitary in response to acute stimulation—acute pain precipitated a rapid depletion of beta-endorphin in the hypothalamus and midbrain. Puig (1982) Anesthesiology 57:1–4, is one of several studies implicating beta-endorphin as a mediator of acute post-operative pain. Terenius (1982) Acta Anaesthesiol. Scand. Suppl. 74:21–24, concluded that endorphins do have a protective role in acute pain after finding that the better the pain control (by higher levels of pain killer after major surgery), the lower the level of beta-endorphin in the cerebral spinal fluid (CSF). Furthermore, beta-endorphin release is a response associated with acute stress, see, e.g., Guilleman (1977) Science 197:1367–1369; Milan (1981) Mod. Probl. Pharmacopsychiatry 17:49–67; Mueller (1981) Life Sci. 29:1169–1176; Vermes (1981) Neurosci. Lett. 27:89–93; Akil (1985) Science 227:424–426; Millan (1985) Int. Rev. Neurobiol. 26:1–83; Millan (1987) J. Neurosci. 7:77–87.

There is academic debate as to whether or not beta-endorphin can control chronic pain. Conflicting theories have been presented as to the role of beta-endorphin in chronic pain. Some studies suggest that beta-endorphin is not involved in chronic pain. For example, Calvino (1992) Pain 49:27–32, found no beta-endorphin response when chronic pain was maximum (in a rat arthritis animal model). Dehen (1990) Rev. Neurol. (Paris) 146:155–157, measuring concentrations of beta-endorphin in the CSF in painless subjects and patients with chronic pain, found no significant difference between the two groups. France (1991) Psychosomatics 32:72–77, found no change in CSF beta-endorphin concentrations after successful treatment of pain and resolution of depression in patients suffering chronic neuralgic low back pain/sciatica. Salar (1991). Pharmacol. Res. 23:181–186, found no difference in levels of beta-endorphin the CSF of control subjects versus patients with different types of chronic pain (i.e., suffering from deafferentation pain syndromes). Guieu (1992) Pain 48:83–88, found that no increase in beta-endorphin levels occurred concomitantly with pain relief (induced by vibration).

In contrast, there are only a few references suggesting beta-endorphin may be a potential analgesic for chronic pain. One early reference, in 1978 (Almay (1978) Pain 5:153–162), suggested that beta endorphin may be involved in chronic pain relief; however, they found that patients classified as having mainly organic pain syndromes were found to have significantly lower CSF endorphin levels than patients with predominantly psychogenic pain. Lipman (1991) Psycho-pharmacology 102:112–116, found that increased levels of CSF beta-endorphin were correlated with increased pain relief in chronic pain patients. Young (1993) J. Neurosurg. 79:816–825, found a direct relationship between beta-endorphin release in the brain and alleviation of intractable chronic pain. Baxter, et al., U.S. Pat. No. 4,350,764, which teaches the recombinant synthesis of beta endorphin in bacteria, states as background that beta endorphin was known to be useful in the treatment of intractable pain, such as phantom limb pain, Significantly, none of these references administers beta endorphin to treat chronic pain.

Thus, it is clear that, to date, there is no consensus concerning the role of beta-endorphin for controlling chronic pain or its ability to selectively modulate between these distinct pain types. Also, before this invention, there was no effective method of specifically treating chronic pain while at the same time not significantly affecting basal nociceptive (acutely painful) responses. The present invention resolves this controversy by providing a novel means to treat chronic pain. Thus, the ability to preserve sensitivity to acute pain while successfully treating chronic pain is a surprising discovery.

SUMMARY OF THE INVENTION

The invention provides a method of treating chronic pain by administering beta-endorphin, wherein basal nociceptive responses are not significantly affected. The beta-endorphin can be administered in the form of an expression cassette, such as an expression vector, for recombinant beta endorphin expression in vivo. The expression vector can be, e.g., any viral vector, such as adenovirus, adeno-associated virus (AAV), lentivirus, or herpes virus, or plasmid, or the like. In a preferred embodiment, the viral vector is a recombinant adenoviral vector or an AAV vector. The beta-endorphin-expressing nucleic acid can be administered by any means, including, e.g., aqueous solutions, lipid-cationic delivery systems, and the like.

In one embodiment, the beta-endorphin-expressing nucleic acid (e.g., an expression cassette, such as a recombinant adenovirus or AAV vector) is administered such that it is transduces a tissue that is anatomically approximate to a nerve, neuron or nerve terminal involved in the transmission or perception of pain, including, e.g., connective tissue (e.g., the epineurium or perineurium), tissue surrounding nerve ganglia, nerve sheathes, nerve linings, or meninges, e.g., the pia mater, or arachnoid or dura membranes; or, cell lining a joint. For example, the recombinant expression systems can be administered to a subarachnoid space or epidural space. In a preferred embodiment, the expression vector is administered into the subarachnoid space. In alternative embodiments, the expression vector is administered in or approximate to joints for, e.g., the treatment of arthritis.

The beta-endorphin-expressing nucleic acid (e.g., recombinant virus or cationic lipid-nucleic acid complex) can be administered in a pharmaceutically acceptable excipient. The pharmaceutically acceptable excipient can be, e.g., an aqueous solution, a lipid delivery system, and the like.

In one embodiment, the beta-endorphin-expressing nucleic acid comprises a nucleic acid encoding a beta-endorphin-secretion signal fusion protein. In alternative embodiments of the method, the nucleic acid insert encoding the beta-endorphin-secretion signal fusion protein is operably linked to a constitutively active promoter to constitutively express the fusion protein, or, it is operably linked to an inducible promoter. The method can further comprising the step of administering a composition capable of inducing the inducible promoter, wherein the fusion protein (e.g., beta-endorphin or a second polypeptide, see below) is expressed upon induction of the promoter.

The recombinant virus concentration in the pharmaceutically acceptable excipient can be between about $10^3$ to about $10^{18}$ particles per mL or can be between about $10^5$ to about $10^{15}$ particles per mL. In a preferred embodiment, the beta-endorphin-expressing nucleic acid comprises a recombinant virus in a pharmaceutically acceptable excipient at a concentration of between about $10^6$ to about $10^{13}$ particles per mL.

Several different expression constructs (e.g., recombinant virii) can be present in the pharmaceutically acceptable excipient. For example, several adenovirus constructs can be co-administered (in a single solution) wherein each constuct contains different forms of beta-endorphin (e.g., various beta-endorphin analogs), different polypeptides (e.g., other pain mediating agents, such as enkaphalin, or markers, such as EGFP, as discussed below), different promoters (e.g., inducible or constitutive), or any combination of polypeptide encoding, transcriptional or translation control or other elements and variations which are apparent to the skilled artisan. In the same manner, different expression vectors can be co-administered, such as, e.g., combinations of adenovirus, AAV, lentivirus, plasmids, and the like.

The virus can be administered into any anatomic area approximate to the spinal chord parenchyma. For example, the virus can be administered into the subarachnoid space or epidurally. After administration the recombinant virus then infects the connective tissue cells surrounding the spinal chord, such as, e.g., the pia mater, arachnoid mater and/or the dura mater. The infected cells express the polypeptide (e.g., the beta-endorphin fusion protein, processed peptide, or fragments of complexes thereof). The fusion protein or a fully processed peptide (e.g., human beta-endorphin peptide) is then secreted. The fusion protein or fragment thereof or a fully processed peptide (e.g., neuroactive peptide) is secreted into the connective tissue interstitial space or cerebral spinal fluid or into (toward) the spinal chord parenchymal tissue in an amount effective to treat chronic pain but not significantly affecting the basal nociceptive responses.

Expression of the in vivo recombinantly generated fusion polypeptide by the transduced connective tissue cells (e.g., pia mater, arachnoid mater, or dura mater cells) results in directed secretion of the fusion protein (or fragment thereof) or a processed peptide into or toward the CSF or the spinal chord parenchymal tissue in an amount effective to treat the chronic pain but not significantly affecting basal nociceptive responses. A similar process occurs when the pharmaceutical composition of the invention is administered into or approximate to a joint space.

In one embodiment of the method, the secretion signal moiety of the fusion protein is a pre-pro sequence of human nerve growth factor (NGF) or any other leader sequence for secretion.

In the methods of the invention the recombinant virus can further comprise a nucleic acid encoding a second polypeptide. The second polypeptide can be the beta-endorphin-secretion signal fusion protein, a partially or fully processed form of beta-endorphin, an analog of beta-endorphin, an enkephalin derived peptide, neurotensin, neuropeptide Y, or fragments or complexes thereof, or enhanced green fluorescence protein (EGFP or eGFP).

In the methods of the invention the nucleic acid encoding the second polypeptide is operatively linked to a promoter different from the promoter to which the beta-endorphin encoding nucleic acid is operatively linked, or, the nucleic acid encoding the second polypeptide is operatively linked to the same promoter the beta-endorphin encoding nucleic acid is operatively linked and the two coding sequences are transcribed as a bicistronic message which is translated to simultaneously produce both polypeptides.

In the methods of the invention the bicistronic message comprises an IRES sequence. The IRES can be the novel IRES of the invention, having a sequence as set forth in SEQ ID NO:4.

The invention also provides a pharmaceutical composition for treating chronic pain, comprising a recombinant virus, such as, e.g., an adenovirus, AAV, lentivirus or herpesvirus, in an excipient pharmaceutically acceptable for in vivo administration, e.g., such as intrathecal or subdural administration. Several different expression constructs (e.g., recombinant virii) can be present in the pharmaceutical compositions of the invention in a variety of combinations as discussed above for pharmaceutically acceptable excipients.

Recombinant virus in the pharmaceutical composition can comprises a nucleic acid insert encoding a beta-endorphin-secretion signal fusion protein. In one embodiment, the recombinant virus (e.g., adenovirus or AAV) concentration in the excipient is between about $10^3$ to about $10^{18}$ particles per mL, or between about $10^5$ to about $10^{15}$ particles per mL or between about 1 6 to about $10^{13}$ particles per mL. The recombinant virus concentration can also be between about $10^3$ to about $10^{18}$ infectious units per mL, or between about $10^5$ to about $10^{15}$ infectious units per mL or between about $10^6$ to about $10^{13}$ infectious units per mL.

When the composition of the invention is administered in an anatomical region approximate to the spinal chord, e.g., intrathecally or subdurally, the recombinant virus (e.g., AAV or adenovirus) infects the meninges, including the pia mater connective tissue cells. The recombinant virus (e.g., AAV or adenovirus), after infecting the connective tissue cells surrounding and/or close to the spinal chord parenchyma (e.g., pia mater), expresses the fusion protein in the infected cell. The infected cell secrets the fusion protein, fragment of the fusion protein or intracellularly processed cleavage product of the fusion protein (e.g., the fully processed peptide) into (or approximate to) spinal chord parenchymal tissue. The fusion protein may be secreted whole but the active moiety is typically the neuroactive peptide or protein that is cleaved (processed intracellularly) from the fusion protein. The leader sequence is usually left behind in the cell. However, the invention includes in vivo synthesis and secretion of all processed, partially processed and unprocessed forms of the polypeptide(s) encoded by the nucleic acids of the pharmaceutial compositions of the invention.

Similarly, recombinant virus, after infecting the connective tissue cells surrounding and/or close joint spaces, is expresses fusion protein in the infected cell and the infected cell secrets the fusion protein or recombinantly generated processed peptide into (or approximate to) the joint space or nerve innervating the joint.

In one embodiment, the nucleic acid insert of the pharmaceutical composition encoding the beta-endorphin-secretion signal fusion protein is operably linked to a constitutively active promoter, wherein the fusion protein is constitutively expressed. In another embodiment, the nucleic acid insert encoding the beta-endorphin-secretion signal fusion protein is operably linked to an inducible promoter, wherein the fusion protein is expressed upon induction of the inducible promoter. The secretion signal moiety of the fusion protein can be a pre-pro sequence of human nerve growth factor (NGF) or any other leader sequence for secretion (see, e.g., Ritty (1999) J. Biol. Chem. 274(13):8933–40; Sasada (1988) Cell Struct. Funct. 13(2):129–41).

The pharmaceutically acceptable excipient can be an aqueous solution, a lipid solution, a mixture thereof, and the like. In the pharmaceutical composition of the invention the pharmaceutically acceptable excipient can be an aqueous solution or a lipid based solution (e.g., including liposomes or cationic or anionic lipid complexes).

In the pharmaceutical composition of the invention the recombinant virus can further comprise a nucleic acid encoding a second polypeptide. The second polypeptide can be any polypeptide or peptide that mediates pain or nerve or neuron function or their supporting tissues, e.g., beta-endorphin-secretion signal fusion protein, a human beta endorphin, an analog of beta-endorphin, an enkephalin derived peptide neurotensin, neuropeptide Y, or fragments or complexes of any of these proteins.

The second polypeptide can also be any marker or identifier (e.g., immunoreactive, with predefined epitope) protein, e.g., any intrinsically fluorescent protein, e.g., enhanced green fluorescence protein (eGFP) and the like.

In the pharmaceutical composition of the invention the nucleic acid encoding the second polypeptide is operatively linked to a promoter different from the promoter to which the beta-endorphin encoding nucleic acid is operatively linked, or, the nucleic acid encoding the second polypeptide is operatively linked to the same promoter the beta-endorphin encoding nucleic acid is operatively linked with and the two coding sequences are transcribed as a bicistronic message which is translated to produce both polypeptides. In the pharmaceutical composition the bicistronic message can comprises an IRES sequence. The IRES can be the novel IRES of the invention having a sequence as set forth in SEQ ID NO:4.

The invention also provides a nucleic acid sequence comprising a sequence as set forth in SEQ ID NO:4, or a nucleic acid sequence consisting essentially of the sequence as set forth in SEQ ID NO:4, or, a nucleic acid sequence having a sequence as set forth in SEQ ID NO:4.

A further understanding of the nature and advantages of the present invention is realized by reference to the remaining portions of the specification, the figures and claims.

All publications, patents and patent applications cited herein are hereby expressly incorporated by reference for all purposes.

BRIEF DESCRIPTION OF THE DRAWINGS

FIG. 4A shows the sequence of the IRES element (SEQ ID NO:4) and its relationship to other elements of the bicistronic message (bicistonic message sequence=SEQ ID NO:5; Kozak consensus sequence=SEQ ID NO:10). FIG. 4B shows the expression cassette used in the bicistronic beta-endorphin- and enhanced fluorescent green protein-expressing AAV vector, described in Example 3, below.

DETAILED DESCRIPTION OF THE INVENTION

Figure 1:
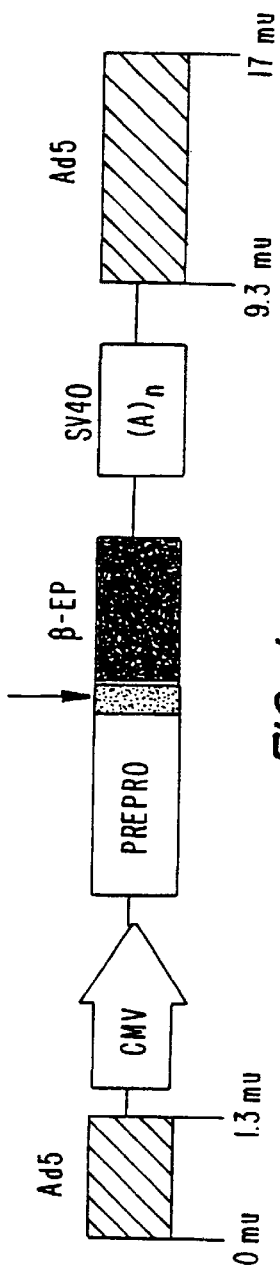
FIG. 1 shows a schematic of the beta-endorphin fusion protein coding sequence as subcloned into a recombinant adenovirus expression vector, described in detail, in Example 1 below.

This invention pertains to the surprising discovery that beta-endorphin can be administered to selectively treat chronic pain, while at the same time not significantly affecting the basal nociceptive responses necessary to perceive acute pain stimuli. In one embodiment, the beta-endorphin is administered in vivo in the form of a beta-endorphin-expressing nucleic acid, such as an expression vector, e.g., a recombinant virus or a plasmid, which can infect or transduce non-dividing connective tissue cells, including, e.g., adenoviruses, adeno-associated viruses (AAVs), lentivirus, herpesvirus, and the like.

Using the compositions and methods of the invention in an appropriate and art-recognized animal model, levels of in vivo generated beta-endorphin were sufficient to significantly desensitize the animals to the hyperalgesia induced by the chronic pain of inflammation. These studies, described in detail in the Examples, below, demonstrate that the compositions and methods of the invention provide a novel gene therapy approach to treating chronic pain. Furthermore, this animal model can be used as described in the Examples to determine that a pharmaceutical is selectively treating chronic pain while at the same time not significantly affecting the ability to perceive protective, acutely painful stimuli.

In this way the animal model can also be used to select beta-endorphin analogues within the scope of the invention, such as, e.g., beta-endorphins with sequence variations that last longer or are more or less potent. The animal model can also be used to select expression systems, e.g., viruses, that can be used to practice the methods of the invention, particularly, to infect non-dividing pia mater cells in vivo.

The invention also provides a recombinant AAV expression vector that expresses a beta-endorphin and a second message. This can be accomplished by incorporation of at least two independent expression modules, i.e, two polypeptide coding sequence each independently, operatively linked to a promoter. Alternatively, this can be accomplished by incorporating a construct encoding a bicistronic message. The message sequence comprises at least one beta-endorphin coding sequence and a second (or more) peptide coding sequence(s). The bicistronic message can express both polypeptides by incorporating an internal ribosomal entry signal (IRES). In one embodiment, the IRES is a novel form of the invention, as discussed below.

The second sequence can be any polypeptide or peptide, including, e.g., a second beta-endorphin coding sequence (which can be the same or a modified version, i.e., a longer or shorter lasting or more or less potent variation of beta endorphin). In other exemplary vectors of the invention (e.g., AAV, adenovirus, or other pia mater infecting virus), the second coding sequence is another pain reducing peptide, either for acute or chronic pain, e.g., an enkephalin derived peptide (i.e., from the prepro-enkephalin gene). Expression of the second gene could control other aspects or forms of pain, e.g., "breakthrough pain." This occurs in situations where there is an acute increase in pain sensation that necessitates additional medication for control. The second polypeptide or message can also enhance the action(s) or half-life or beta-endorphin. The second polypeptide can be any factor which mediates pain, neuron physiology or growth or their supporting tissues, e.g., (in addition to beta endorphin and analogs) enkephalin, neurotensin, neuropeptide Y, or fragments or complexes.

The second sequence can also encode a polypeptide or message used to monitor the bio-distribution and expression of the recombinant virus, e.g., any cell marker system can be used. The longevity of expression of the virus after administration can also be determined using such a "marker" polypeptide or message.

The coding sequences can be operatively linked to constitutively active or to inducible promoters or to any combination thereof, thus allowing design of an expression cassette that can be induced to express beta-endorphin(s) and/or other polypeptides independently at different times and at different levels.

Figure 4:
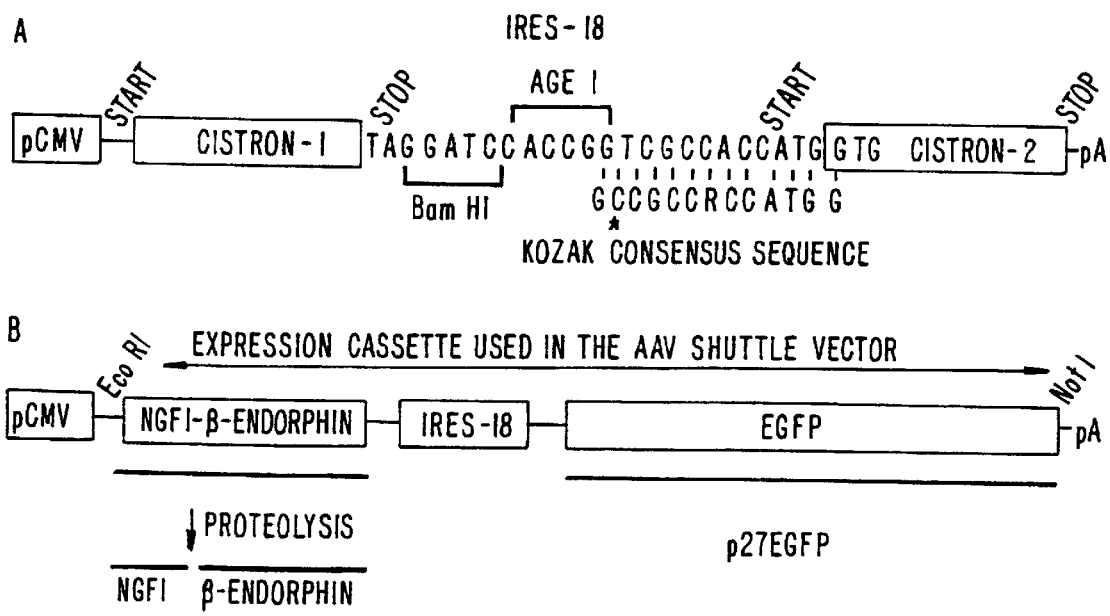
FIG. 4 shows a schematic of a dicistronic AAV-beta endorphin expressing recombinant AAV expression vector which incorporates a novel internal. ribosome entry signal (IRES) element, described in detail, below.

The invention also provides a novel internal ribosomal entry (or re-entry) sequence (IRES). The IRES of the invention (SEQ ID NO:4), or "IRES-18," is the most compact artificial intercistronic IRES described. IRES-18 is void of any start (ATG) codon. While short (the average length of a viral IRES is about 400 to 1000 base pairs, see, e.g., Hellen (1995) Curr. Top. Microbiol. Immunol. 203:31–63; Scheper (1994) FEBS Lett. 352(3):271–5; Jang (1990) Enzyme 44(1–4):292–309), IRES-18 is lengthy enough to function as an internal ribosomal re-entry sequence after any of the stop codons (TAG, TGA, and TAA) finishing the first cistron of a message (i.e., transcript). IRES-18 has a homology domain to the Kozak's motif, as it is indicated in FIG. 4A. Importantly, the downstream region of IRES-18, in front of the second cistron, is in conformity with the eukaryotic consensus Kozak sequence 5'-GCCGCCRCCAUGG-3' (SEQ ID NO:8), where the purine (R) at −3 in IRES-18 (SEQ ID NO:4) is A, and the codon following the AUG start codon in the EGFP identical with the G found in the Kozak's motif (see also J Cell Biol, 108 (1989) 229–241). The IRES relieves the need for complicated in frame recombinant vector (transgene) protein fusions to produce functional proteins from a single bicistronic message (see, e.g., Li (1997) Biotechniques 23(5):874–8, 880, 882.).

DEFINITIONS

To facilitate understanding the invention, a number of terms are defined below.

The term "administering" incorporates the common usage and refers to any appropriate means to give a pharmaceutical to a patient, taking into consideration the pharmaceutical composition and the preferred site of administration (e.g., in a preferred embodiment, the pharmaceutical composition of the invention is injected into the subarachnoid space as an aqueous solution).

The term "basal nociceptive responses" incorporates its common usage and refers to baseline responses to nociceptive, or painful, stimuli.

The terms "chronic pain" and "acute pain" incorporate their common usages; subjective (e.g., clinical diagnosis) and objective means (e.g., laboratory tests, PET) to determine the presence of chronic pain and/or acute pain, and to distinguish between these two distinct categories of pain, are described in detail, below.

The term "beta-endorphin" incorporates its common usage and refers to a family of analgesic opioid peptides which, in nature, are secreted by the mammalian pituitary gland, and all biologically active analogs, as described in detail, below. The term "analog" refers to a polypeptide, such as the beta endorphin of the invention, which has a modified amino acid sequence, such that the change(s) do not substantially alter its structure and activity. Thus, a polypeptide analog is within the scope of the invention if it has the same biological activity as beta endorphin, as described below. For example, conservative substitution tables providing functionally similar amino acids are well known in the art are used to make beta-endorphin analogs used in the invention; e.g., one exemplary guideline to select conservative substitutions includes (original residue followed by exemplary substitution): ala/gly or ser; arg/lys; asn gln or his; asp/glu; cys/ser; gln/asn; gly/asp; gly/ala or pro; his/asn or gln; ile/leu or val; leu/ile or val; lys/arg or gin or glu; met/leu or tyr or ile; phe/met or leu or tyr; ser/thr; thr/ser; trp/tyr; tyr/trp or phe; val/ile or leu. The exemplary animal model described herein can be used to select appropriate beta-endorphin analogues.

The term "enkephalin" incorporates its common usage and refers to a family of opioid analgesic peptides, and all biologically active analogs, which can be designed and selected as described for beta-endorphin, as noted above. For example, Endomorphin-1 and endomorphin-2 are tetrapeptides whose binding profiles and analgesic activities indicate that they are endogenous ligands at mu opioid receptors, see, e.g., Sanchez-Blazquez (1999) J. Pharmacol. Exp. Ther. 291(1):12–18). See also, Danielson (1999) Gen. Comp. Endocrinol. 113(2):169–86. The terms "neurotensin" and "neuropeptide Y" also incorporate their common usages; see, e.g., Vincent (1999) Trends Pharmacol. Sci. 20(7):302–9; Nordmann (1999) Eur. J. Biochem. 261(1):216–26.

The term "hyperalgesia" refers to an increased response to a stimulus that is normally painful (see, e.g., Bonica (1990) infra). Its presence is recognized as a symptom of chronic pain (i.e., its presence is associated with or is a sequelae of chronic pain).

The term "internal ribosomal entry signal" or "internal ribosomal re-entry signal" or "IRES" incorporates the common usage and refers to a sequence that promotes 'internal' entry of ribosomes onto a message (i.e., transcript) independent of the typical ribosomal entry signal, the non-capped 5' end of an mRNA; see, e.g., Jang (1990) supra. The invention provides a novel IRES sequence (SEQ ID NO:4) that is significantly shorter than conventional, typically viral, IRES elements, see FIG. 4A.

The term "nucleic acid" incorporates the common usage and refers to a deoxyribonucleotide or ribonucleotide in either single- or double-stranded form. The term nucleic acid includes and is used interchangeably with gene, cDNA, mRNA, oligonucleotide primer, probe and amplification product.

The term "pharmaceutically acceptable excipient" incorporates the common usage and refers to includes any suitable pharmaceutical excipient, including, e.g., water, saline, phosphate buffered saline, Hank's solution, Ringer's solution, dextrose/saline, glucose, lactose, or sucrose solutions, magnesium stearate, sodium stearate, glycerol monostearate, glycerol, propylene glycol, ethanol, and the like.

The term "pre-pro sequence" incorporates the common usage and refers to an amino acid sequence containing two domains: a pre-sequence, which is synonymous with "signal peptide," and a "pro-sequence."

The term "pia mater connective tissue" incorporates the common usage refers to the tissue, membrane, or connective tissue which separates the parenchyma of the spinal cord from the subarachnoid space (the cerebral spinal fluid (CSF) space).

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant "expression cassettes" which contain only the minimum elements (e.g., a promoter) needed for transcription of the recombinant nucleic acid.

The term "recombinant adenovirus" incorporates the common usage refers to any adenovirus of the family Adenoviridae, including, e.g., the genus Mastadenovirus, capable of infecting non-dividing mammalian cells, particularly, connective tissue cells, such as cells of the pia mater; see, e.g., Kovesdi (1997) Curr. Opin. Biotechnol. 8:583–589; Robbins (1998) Trends Biotechnol. 16:35–40.

The term "subarachnoid space" or cerebral spinal fluid (CSF) space incorporates the common usage refers to the anatomic space between the pia mater and the arachnoid membrane containing CSF.

The term "spinal cord parenchymal tissue" incorporates the common usage and refers to the body of the spinal cord containing nerve tissue, e.g., white and gray mater.

The term "treating" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; slowing in the rate of degeneration or decline; making the final point of degeneration less debilitating; improving a patient's physical or mental well-being; or, in some situations, preventing the onset of the symptom or condition, e.g., pain. The treatment or amelioration of symptoms can be based on any objective or subjective parameter; including, e.g., the results of a physical examination and/or a psychiatric evaluation, or, simply an improvement in the patient's sense of well-being. For example, the methods of the invention selectively treats chronic pain by ameliorating the hyperalgesia associated with chronic pain, while not significantly affecting basal nociceptive responses.

Distinguishing Chronic from Acute Pain

Pain is always subjective and can have physiologic, pathophysiologic, psychologic, emotional, and affective dimensions. Pain causation can be broadly categorized as organic or psychogenic. Basically, two types of pain exist— acute pain and chronic pain. Each possibly is mediated by anatomically different nerves. Each type of pain has a different physiologic role. For example, the ability to perceive and respond to "acutely" painful stimuli, which usually has the potential to cause tissue damage, serves a protective role for the individual. While many treatments for acute pain cannot ameliorate chronic pain (this, in fact, is used as one means to objectively identify "chronic" versus "acute" pain, as discussed below), before this invention, there existed no effective therapies to treat chronic pain without the unwanted side effect of significantly dampening protective acute pain responses.

Diagnosing and Assessing Chronic Pain

The invention provides methods of treating chronic pain while at the same time not significantly affecting the ability to respond to acutely painful, and potentially harmful, stimuli. Thus, proper diagnosis of chronic pain is necessary both to practice and to assess the success of the compositions and methods of the invention. Means to diagnosis chronic pain include classical clinical and psychological evaluations, which can be augmented by various laboratory procedures, as described herein. Such means are well-described in the medical/scientific and patent literature; some illustrative examples are provided below.

One criteria to diagnose a "chronic" pain is whether the pain persists for a month beyond the usual course of an acute disease or a reasonable time for an injury to heal. This evaluation is made by the clinician on a case by case basis. Acute diseases or injuries can heal in 2, 3, or, at most, 6 weeks, depending on the nature of the condition or injury, the age and health of the patient, and the like. Clinicians are trained to be very aware of this "acute" versus "chronic" pain distinction, for it is critical to make correct diagnosis and treatment plans. For example, a simple wrist fracture can remain painful for a week to ten days; however, if pain persists longer than this period, a dystropathy could be developing which will be irreversible if not treated. See, e.g., Bonica, et al., (1990) "Management of Pain," 2nd Ed., Vol. 1, Lea & Feibiger, Philadelphia, Pa.; Wall and Melzack (1994) "Textbook of Pain," Churchill Livingstone, N.Y. Accordingly, a chronic pain is diagnosed by the practitioner based on clinical and laboratory results, depending on the particular condition or injury, patient, and the like (see also, e.g., Russo (1998) Annu. Rev. Med. 49:123–133).

Another means to identify a "chronic" pain is by diagnosis of a pathologic process (which is usually also chronic) known to produce or be associated with chronic pain. Such conditions are well characterized and include, e.g., chronic pain syndrome (see, e.g., Clifford (1993) Can. Fam. Physician 39:549–559), arthralgia, arthritis (e.g., osteoarthritis and rheumatoid arthritis), causalgia, hyperpathia, neuralgia, neuritis, radiculagia, fibromyalgia (see, e.g., Simms (1998) Am. J. Med. Sci. 315:346–350), orofacial pain and temporomandibular disorders (see, e.g., Bindeman (1997) Curr. Opin. Periodontol. 4:144–15), reflex sympathetic dystrophy (see, e.g., Dangel (1998) Paediatr. Anaesth. 8:105–112, chronic back pain, certain cancers, and the like.

Chronic pain is also associated with particular injuries to the nerves. These include, e.g., nerve transection (traumatic or surgical), chronic abnormal pressure on a nerve, chemical (e.g., formalin) destruction of nerve tissue, and the like.

Chronic pain can also be distinguished from acute pain by its non-responsiveness to pharmacologic therapies known to significantly ameliorate or abate acute pain. When pain is initially diagnosed as acute or of unknown etiology, the clinician typically administers one of several analgesics known in the art to be effective for acute pain, such as, e.g., a non-steroid anti-inflammatory drug (NSAID), such as, e.g., aspirin, ibuprofen, propoxyphene, tramadol, acetaminophen and the like (see, e.g., Tramer (1998) Acta Anaesthesiol. Scand. 42:71–79). If there is no significant amelioration of pain, as assessed by the clinician, over an approximately six week period, then a provisional diagnosis of chronic pain can be made. Ultimately, as discussed above, a diagnosis of chronic pain depends upon determination as to whether pain would be expected, given each individual situation.

Other treatments to which chronic pain is also typically incompletely or totally unresponsive include tricyclic antidepressant administration, psychotherapy, or alternative medicines, such as acupuncture, biofeedback, and the like.

Laboratory, radiographic and other types of imaging procedures can also be used to diagnose chronic pain. In particular, positron emission tomography, or PET, now allows the clinician to objectify such otherwise merely subjective symptoms, including chronic pain (see, e.g., Reiss (1998) Fortschr. Med. 116:40–43; Di Piero (1991) Pain 46:9–12).

Endorphins for Treating Chronic Pain

The invention provides for methods of treating chronic pain utilizing recombinantly expressed beta endorphin, wherein the beta endorphin is recombinantly generated in vivo via transformation of pia mater cells by adenoviral expression vectors. General methods to practice the invention are well described in the scientific and patent literature. A few illustrative examples are set forth below.

Beta Endorphin Analogues

The invention includes expression of a sequence the same or similar to naturally occurring beta-endorphin, which is a fragment of the beta-lipotropin portion of the ACTH/beta-endorphin precursor protein, a pituitary hormone. It is cleaved to form a 31 amino acid long biologically active beta-endorphin peptide, see, e.g., U.S. Pat. No. 4,105,652, and U.S. Pat. No. 4,313,937. Similarly, the compositions and methods of the invention incorporate all structural conservative variants of beta-endorphin which are biologically active and can be recombinantly produced, see, e.g., U.S. Pat. No. 4,081,434; U.S. Pat. No. 4,116,950; U.S. Pat. No. 4,350,764; U.S. Pat. No. 4,469,631; and Van Nispen, et al, EP 0417819. These variations include fusion proteins comprising beta-endorphin and additional peptide domains, such as secretion signals, epitope tags, and the like, as described below. See also U.S. Pat. No. 4,098,778, U.S. Pat. No. 4,250,087; U.S. Pat. No. 4,317,770; U.S. Pat. No. 4,312,857; U.S. Pat. No. 4,330,465; and U.S. Pat. No. 4,422,968.

Identifying Beta Endorphin Analogues

Any biologically active, recombinantly expressible beta-endorphin can be used in the compositions and methods of the invention for the treatment of chronic pain, in addition to the compounds and compositions described and incorporated by reference herein. Furthermore, additional useful beta endorphin analogues useful for practicing the invention can be determined by the skilled artisan. A variety of Oh routine, well-known methods can be used and are described in the scientific and pain literature. They include in vitro and in vivo assays for the identification of biologically active beta-endorphin analogues. A few illustrative examples are described below.

Well-known and art-recognized assays that can be used to identify biologically active, analgesic beta-endorphin analogues useful in the invention include, e.g., the foot-withdrawal, tail-flick and hot-plate tests, see, e.g., Cepeda-Benito (1998) Exp. Clin. Psychopharmacol. 6:248–254; Fang (1998) Brain Res. 790:14–24; Szekely (1997) Eur. J. Pharmacol. 336:143–154; U.S. Pat. No. 4,422,968. A model of testing for chronic pain. analgesia in the rat is the adjuvant-induced arthritis test, see, e.g., Millan (1986) J. Neurosci. 6:899–906; and Calvino (1992) Pain 49:27–32. Another model includes the ability to ameliorate hyperalgesia, see, e.g., Xu (1997) Cytokine 9:1028–1033.

Biologically active beta-endorphin analogs can also be assessed by ligand (e.g., receptor) binding assays, as described, e.g., by Ferrara (1979) Biochem. Biophys. Res. Commun. 89:786–792; Hammonds (1981) Anal. Biochem. 114:75–84; Loh (1983) Proc. West Pharmacol. Soc. 26:305–307; Hammonds (1981) Biochem. Biophys. Res. Commun. 98:211–218; U.S. Pat. No. 4,219,468, U.S. Pat. No. 4,250,087. Finally, under the appropriate conditions and approvals, biologically active beta-endorphin analogs can also be assessed in patients for their ability to ameliorate pain, see, e.g., Donovan (1997) Transplantation 63:1423–1429.

Nucleic Acids and Expression Vectors

This invention provides pharmaceutical compositions comprising beta endorphin expressing nucleic acids, e.g., recombinant viruses, e.g., adenovirus, in an pharmaceutically acceptable excipient. The invention also provides methods of using these pharmaceutical compositions to treat chronic pain while not significantly affecting the ability to perceive acutely painful stimuli. The invention can be practiced in conjunction with any method or protocol known in the art, which are well described in the scientific and patent literature. Therefore, only a few general techniques will be described prior to discussing specific methodologies and examples relative to the novel reagents and methods of the invention.

General Techniques

Nucleic acids for making or using the pharmaceutical compositions of this invention, whether RNA, cDNA, genomic DNA, or hybrids thereof, may be isolated from a variety of sources, genetically engineered, and/or expressed recombinantly. Alternatively, these nucleic acids can be chemically synthesized in vitro (see definition of nucleic acids). Techniques for the manipulation of nucleic acids, such as, e.g., subcloning into expression vectors, labeling probes, sequencing DNA, DNA hybridization are described in the scientific and patent literature, see e.g., Sambrook, ed., *Molecular Cloning: A Laboratory Manual* (2nd ed.), Vols. 1–3, Cold Spring Harbor Laboratory, (1989) ("Sambrook"); *Current Protocols in Molecular Biology*, Ausubel, ed. John Wiley & Sons, Inc., New York (1997) ("Ausubel"); and, *Laboratory Techniques in Biochemistry and Molecular Biology: Hybridization with Nucleic Acid Probes*, Part I. Theory and Nucleic Acid Preparation, Tijssen, ed. Elsevier, N.Y. (1993) ("Tijssen"). Product information from manufacturers of biological reagents and experimental equipment also provide information regarding known biological methods. Such manufacturers include, e.g., the SIGMA chemical company (Saint Louis, Mo.), R&D systems (Minneapolis, Minn.), Pharmacia Biotech (Piscataway, N.J.), Clontech Laboratories, Inc. (Palo Alto, Calif.), Aldrich Chemical Company (Milwaukee, Wis.), GLBCO BRL Life Technologies, Inc. (Gaithersburg, Md.), Fluka Chemica-Biochemika Analytika (Fluka Chemie AG, Buchs, Switzerland), Applied Biosystems (Foster City, Calif.), as well as many other commercial sources known to one of skill.

Nucleic acids for making or using the invention can also be generated or quantitated using amplification techniques. Suitable amplification methods include, but are not limited to: polymerase chain reaction, PCR (*PCR Protocols, A Guide to Methods and Applications*, ed. Innis, Academic Press, N.Y. (1990) and PCR STRATEGIES (1995), ed. Innis, Academic Press, Inc., N.Y. (Innis)), ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. USA, 86:1173); and, self-sustained sequence replication (Guatelli (1990) Proc. Natl. Acad. Sci. USA, 87:1874); Q Beta replicase amplification (Smith (1997) J. Clin. Microbiol. 35:1477–1491, automated Q-beta replicase amplification assay; Burg (1996) Mol. Cell. Probes 10:257–271) arid other RNA polymerase mediated techniques (e.g., NASBA, Cangene, Mississauga, Ontario); see also Berger (1987) Methods Enzymol. 152:307–316, Sambrook, Ausubel, Mullis (1987) U.S. Pat. Nos. 4,683,195, and 4,683,202; Arnheim (1990) C&EN 36–47; Lomell J. Clin. Chem., 35:1826 (1989); Van Brunt (1990) Biotechnology, 8:291–294; Wu (1989) Gene 4:560; Sooknanan (1995) Biotechnology 13:563–564; Methods for cloning in vitro amplified nucleic acids are described in Wallace, U.S. Pat. No. 5,426,039.

Nucleic acids and proteins (e.g., the recombinant beta-endorphin fusion protein expressed in vivo) are detected and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, Dot-blot analysis, gel electrophoresis (e.g., SDS-PAGE), RT-PCR, quantitative PCR, other nucleic acid or target or signal amplification methods, radiolabeling, scintillation counting, and affinity chromatography.

Recombinant Beta-Endorphin-Encoding Nucleic Acid

The invention provides recombinant beta-endorphin expressed in vivo. In one embodiment, the nucleic acid is administered using an expression vector, e.g., a recombinant adenovirus vector, capable of transducing (infecting) nerve connective tissue cells (e.g., pia mater connective tissue cells). In one embodiment, the beta-endorphin is secreted as a beta-endorphin fusion protein. Nucleic acids encoding beta-endorphin and structural variations of beta-endorphin which are biologically active and can be recombinantly produced are well known in the art and have been described, e.g., U.S. Pat. No. 4,081,434; U.S. Pat. No. 4,116,950; U.S. Pat. No. 4,350,764; U.S. Pat. No. 4,469,631; and Van Nispen, et al, EP 0417819.

In the expression vector, beta-endorphin fusion protein coding sequences are operatively linked to "control elements" or "transcriptional regulatory sequences." These systems can be manipulated to vary in their strength and specificities. They can include non-translated sequences, e.g., enhancers, promoters, and 3' untranslated regions which interact with host cellular proteins to carry out transcription and translation. Depending on the particular expression cassette or vector system, any number of suitable transcription and translation elements, including constitutive, inducible or cell specific promoters, may be used.

In mammalian systems, especially vectors for expression in humans in vivo, promoters from the mammalian genes or from mammalian viruses are most appropriate. Examples of constitutive promoters include elements from mammalian viruses such as, e.g., cytomegalovirus (CMV), rous sarcoma virus, simian virus 40, Moloney murine leukemia virus, see, e.g., Bui (1997) Hum. Gene Ther. 8:2173–2182; Qin (1997) Hum. Gene Ther. 8:2019–2029. Example of inducible promoters include, e.g., tetracycline-regulated promoters, see, e.g., Massie (1998) J. Virol. 72:2289–2296; glucocorticoid-responsive promoter, see, e.g., Narumi (1998) Blood 92:822–833. An examples of cell-specific promoters include, e.g, the nerve specific promoter of the peripheral myelin protein 22 gene, see, e.g., Nelis (1998) J. Med. Genet. 35:590–593. The promoters or other transcriptional regulatory elements used in this invention can be isolated from natural sources, obtained from such sources as ATCC or GenBank libraries, or prepared by synthetic or recombinant methods, as described herein.

Typical expression systems contain, in addition to coding sequence and transcriptional regulatory elements, transcription and translation terminators, polyadenylation sequences, transcription and translation initiation sequences. The expression systems optionally contain at least one independent terminator sequence, sequences permitting replication of the cassette both in vitro and in vivo, e.g., eukaryotes or prokaryotes, or a combination thereof, (e.g., shuttle vectors) and selection markers for the selected expression system, e.g., prokaryotic or eukaryotic systems.

Recombinant Fusion Proteins: Signal Sequences

In the compositions and methods of the invention, the recombinant virus, after intrathecal administration, transduces a tissue that is anatomically approximate a nerve involved in the transmission or perception of pain, including, e.g., connective tissue (e.g., the epineurium or perineurium), tissue surrounding nerve ganglia, nerve sheathes, nerve linings, or meninges, e.g., the pia mater, or arachnoid or dura membranes. In a preferred embodiment, the expression vector is administered into the subarachnoid space for the infection of meninges, particularly, pia mater cells. In alternative embodiments, the expression vector is administered in or approximate to joints for, e.g., the treatment of chronic pain associated with arthritis.

These transduced (infected) cells express the beta endorphin fusion protein. When pia mater cells are transduced, the fusion protein is secreted into the spinal cord parenchymal tissue in an amount effective to treat chronic pain. To effect the secretion of the beta-endorphin peptide, e.g., by the pia mater connective tissue cells, it is expressed as a recombinant beta-endorphin-secretion signal fusion protein. Any mammalian secretion signal can be used, and many are well known in the art, see, e.g., Lo (1998) Protein Eng. 11:495–500; Kurepa (1998) J. Exp. Med. 188:973–978; Liu (1997) Gene 203:141–148; Ueno (1997) Arterioscler. Thromb. Vasc. Biol. 17:2453–2460. In one embodiment, the secretion signal moiety of the fusion protein is a pre-pro sequence of human nerve growth factor (NGF), see, e.g., Beutler (1995) J. Neurochem. 64:475–481.

Adenovirus Vectors for Expressing Recombinant Beta Endorphins In vivo

In one embodiment, the beta-endorphin fusion protein of the invention is cloned in an adenoviral vector suitable for gene therapy, i.e., expression in vivo. Adenoviral vectors are well-known to be suitable means to transduce non-dividing cells in vivo to effect the expression of recombinant polypeptides. The use of adenoviral vectors in vivo, and for gene therapy, is well described in the patent and scientific literature, e.g., see, Hermens (1997) J. Neurosci. Methods., Jan., 71(1): 85–98; Zeiger (1996) Surgery 120:921–925; Cannon (1996) Cardiovasc Res. 32:962–972; Huang (1996) Gene Ther. 3:980–987; Zepeda (1996) Gene Ther. 3:973–979; Yang (1996) Hum. Mol. Genet. 5:1703–1712; Caruso (1996) Proc. Natl. Acad. Sci. USA 93:11302–11306; Rothmann (1996) Gene Ther. 3:919–926; Haecker (1996) Hum. Gene Ther. 7:1907–1914; to name just a few. The use of adenoviral vectors is also described in, e.g., U.S. Pat. No. 5,792,453; U.S. Pat. No. 5,731,172; U.S. Pat. No. 5,670,488; U.S. Pat. No. 5,585,362. Adenovirus type 5 and adenovirus type 2 genomes are described, e.g., by Chroboczek (1992) Virology 186:280–285.

Adenovirus vectors for gene therapy are typically made replication defective by deletion of adenovirus early ("E") region 1 ("E1") region genes. For isolation, propagation, and large-scale production of such vectors, E1 functions are supplied in trans from a stable cell line. Typically, adenovirus vectors used for clinical studies are produced in the 293 cell, a human embryonic kidney cell line expressing E1 functions from an integrated segment of the left end of the adenovirus (Ad) type 5 (Ad5) genome (see, e.g., Hehir (1996) J. Virol. 70:8459–8467) (other cell lines can be used for the propagation of early region 1-deleted adenoviral vectors, e.g., the human embryonic retinoblast (HER) line 911, with a plasmid containing base pairs 79–5789 of the Ad5 genome, see Fallaux (1996) Hum. Gene Ther. 7:215–222). Many adenoviral vectors are engineered such that the inserted gene of interest (e.g., a beta-endorphin fusion protein transgene) replaces the adenovirus E1a, E1b, and E3 genes; subsequently the replication-defective vector can be propagated only in human 293 cells that supply the deleted E1 gene functions in trans. Alternatively, adenoviral E1, E3, and the E2b gene functions can be deleted (see, e.g., Amalfitano (1998) J. Virol. 72:926–933); or, the E1 and/or E4 genes can be deleted (see, e.g., Brough (1996) J. Virol. 70:6497–6501; Armentano (1995) Hum. Gene Ther. 6:1343–1353). Adenoviral vectors can also contain a deletion in the adenovirus early region 3 and/or early region 4.

Alternatively, to achieve amplification of recombinant replication defective adenoviral transgene expression in vivo, a.the trans complementation approach can be used, where cotransduction of an E1-defective adenovirus with a plasmid containing the deleted E1 functions into cells results in E1-defective virus production by those cells (see, e.g., Dion (1996) Cancer Gene Ther. 3:230–237; Goldsmith (1994) Hum. Gene Ther. 5:1341–134).

Adenoviral vectors can also include a deletion of some or all of the protein IX gene (four trimers of Ad protein IX are embedded in the upper surface of viral hexons to create a highly-stable assembly, see, Babiss (1991) J. Virol. 65:598–605; Furcinitti (1989) EMBO J. 8:3563–3570) (for Ad pIX deletion vectors, see, e.g., Krougliak (1995) Hum. Gene Ther. 6:1575–1586). Adenoviral vectors can also include deletions of the E1a and/or E1b sequences.

Adeno-Associated Virus (AAV)-Based Vectors

Adeno-associated virus (AAV)-based vectors can also used to transduce cells with beta-endorphin expressing nucleic acids. See, Okada (1996) Gene Ther. 3:957–964; West (1987) Virology 160:38–47; Carter (1989) U.S. Pat. No. 4,797,368; Carter et al. WO 93/24641 (1993); Kotin (1994) Human Gene Therapy 5:793–801; Muzyczka (1994) J. Clin. Invest. 94:1351, for an overview of AAV vectors. Construction of recombinant AAV vectors are described in a number of publications, including Lebkowski, U.S. Pat. No. 5,173,414; Tratschin (1985) Mol. Cell. Biol. 5(11) :3251–3260; Tratschin (1984) Mol. Cell. Biol. 4: 2072–2081; Hermonat (1984) Proc. Natl. Acad. Sci. USA 81: 6466–6470; McLaughlin (1988) and Samulski (1989) J. Virol., 63:03822–3828. Cell lines that can be transformed by rAAV include those described in Lebkowski (1988) Mol. Cell. Biol., 8:3988–3996. See also Xiao (1998) J. Virol. 72(3):2224–32, describing a useful AAV helper plasmid and generation of high titers of infectious AAV.

Lentivirus-Based Vectors

Lentiviral vectors are also effective vehicles for the delivery and stable expression of genes in nondividing primary cells, e.g., connective tissue cells, e.g., pia mater or dura mater or arachnoid mater cells. See, e.g., Unutmaz (1999) J. Exp. Med. 189(11):1735–46. See also von Ruden (1995) Biotechniques 18(3):484–9, describing generation of high-titer, helper-free retrovirus vectors employing receptor-mediated, adenovirus-augmented transfection into standard packaging cell lines. The vectors are optionally pseudotyped to extend the host range of the vector to cells which are not infected by the retrovirus corresponding to the vector.

Other Viral Vectors for Expressing Recombinant Beta Endorphins In Vivo

Retroviral vectors can also be used to express the beta-endorphin expressing nucleic acid in vivo. These include recombinant vectors based upon murine leukemia virus (MuLV), gibbon ape leukemia virus (GaLV), Simian Immuno deficiency virus (SIV), human immuno deficiency virus (HIV), and combinations thereof. See, e.g., Buchscher (1992) J. Virol. 66(5) 2731–2739; Johann (1992) J. Virol. 66 (5):1635–1640 (1992); Sommerfelt (1990) Virol. 176:58–59; Wilson (1989) J. Virol. 63:2374–2378; Miller (1991) J. Virol. 65:2220–2224; Wong-Staal et al., PCT/US94/05700, and Rosenberg and Fauci (1993) in Fundamental Immunology, Third Edition Paul (ed) Raven Press, Ltd., New York and the references therein, and Yu (1994) supra). Arai (1998) J. Virol. 72(2):1115–21, describing production of high-titer vesicular stomatitis virus G protein (VSV-G)-pseudotyped retrovirus vectors. Other suitable viral vectors include herpes virus (see, e.g., Aurelian (1999) Vaccine 17(15–16):1951–63), cytomegalovirus (see, e.g., Tumilowicz (1990) In Vitro Cell Dev. Biol. 26(12):1144–50) and vaccinia virus.

Formulation and Administration Pharmaceuticals

Nucleic acids encoding beta endorphins and fusion proteins are formulated as pharmaceuticals to be used in the methods of the invention to treat chronic pain by gene therapy. The nucleic acid can be in the form of a beta-endorphin-encoding expression cassette, such as an expression vector. However, the beta-endorphin-expressing nucleic acid can be administered by any means in any appropriate formulation, including, e.g., are formulated as pharmaceuticals comprising lipid-cationic delivery systems.

In one embodiment, a recombinant vector (e.g., an adenoviral or AAV vector) containing a coding sequence for a beta-endorphin fusion protein is injected intrathecally, resulting in infection of meningeal (including dura and arachnoid membranes) and pia mater cells which are anatomically approximate to the site of the injection. The recombinant vector can be injected in an site anatomically approximate to the spinal chord parenchyma, including e.g. the intrathecal space or subdurally.

The recombinant beta-endorphin is designed as part of a fusion protein containing secretion signals. Thus, the beta-endorphin is secreted into (approximate to) the parenchyma of the spinal cord (and the CSF) by the infected connective tissue (e.g., pia mater) cells.

Routine means to determine drug regimens and formulations to practice the methods of the invention are well described in the patent and scientific literature, and some illustrative examples are set forth below. For example, details on techniques for formulation and administration are well described in the scientific and patent literature, see, e.g., the latest edition of Remington's Pharmaceutical Sciences, Maack Publishing Co, Easton Pa.

The pharmaceutical composition of the invention is administered such that the beta-endorphin expressing nucleic acid transduces a tissue that is anatomically approximate a nerve, including, e.g., epineurium or perineurium, tissue surrounding nerve ganglia, nerve sheathes, nerve linings, or meninges, e.g., the pia mater, or arachnoid or dura membranes. In a preferred embodiment, the pharmaceutical composition is administered into the subarachnoid space to infect connective tissue, e.g., pia mater, cells. In alternative embodiments, the pharmaceutical composition is administered in or approximate to joints for, e.g., the treatment of chronic pain associated with arthritis.

In a preferred embodiment, the pharmaceutical composition is administered intrathecally (i.e., into the CSF in the subarachnoid space), where the concentration of recombinant virus in the pharmaceutically acceptable excipient is between about $10^3$ to about $10^{18}$ particles per mL, or between about $10^5$ to about $10^{15}$ particles per mL, or between about $10^6$ to about $10^{13}$ particles per mL. The virus can be in an appropriate aqueous or a lipid a based solution.

Aqueous suspensions of the invention can also include any excipients or admixture suitable for the manufacture of aqueous suspensions. The aqueous suspension can also contain one or more preservatives, such as ethyl or n-propyl p-hydroxybenzoate. The aqueous suspension can be adjusted for osmolarity. The aqueous solution can be adjusted to promote the stability of the vector for lyophilization. For example, a cryoprotectant solution that can significantly maintain viral stability after freeze-thaw cycles or lyophilization includes 0.5 M sucrose, 0.5 M trehalose, and 10% sorbitol/0.4% gelatin, see, e.g., Croyle (1998) Pharm. Dev. Technol. 3:373–383.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM–50 mM histidine, 0.1%–2% sucrose, 2%–7% mannitol at a pH range of 4.5 to 5.5, that is combined with the appropriate aqueous buffer prior to use.

After a pharmaceutical comprising a recombinant virus (e.g., an AAV or adenovirus) of the invention has been formulated in an acceptable carrier/excipient, it can be placed in an appropriate container, e.g., as a kit, and labeled for treatment of the indicated condition. For administration of the pharmaceutical compositions of the invention, such labeling would include, e.g., instructions concerning the amount, frequency and method of administration. These instructions can also be part of a kit.

Cationic Lipid-Nucleic Acid Formulations

The beta-endorphin encoding nucleic acids of the invention can also be formulated as cationic lipid-nucleic acid compositions administration in a variety of ways. Details on techniques for formulation and administration are well described in the scientific and patent literature, see, e.g., the latest edition of "Remington's Pharmaceutical Sciences" (Maack Publishing Co, Easton Pa.). See also, Lasic and Templeton (1996) Adv. Drug Deliv. Rev. 20: 221–266 and references cited therein. The ratios of each component in the cationic lipid-nucleic acid complexes, final concentrations, buffer solutions, and the like can be readily optimized by the skilled artisan, taking into consideration the mode of delivery (i.e., intrathecal, intra-articular), the anatomical site of delivery, any existent conditions or diseases, the condition and age of the patient, and the like.

Cationic lipid carriers can contain a positively charged lipid and a neutral lipid, usually they will be in approximately equimolar amounts. The neutral lipid is helpful in maintaining a stable lipid bilayer in liposomes, and can significantly affect transfection efficiency. The liposomes may have a single lipid bilayer (unilamellar) or more than one bilayer (multilamellar). They are generally categorized according to size, where those having diameters up to about 50 to 80 nm are termed "small" and those greater than about 80 to 1000 nm, or larger, are termed "large." Thus liposomes are typically referred to as large unilamellar vesicles (LUVs), multilamellar vesicles (MLVs) or small unilamellar vesicles (SUs). Methods of producing cationic liposomes are known in the art. See, e.g., Liposome Technology (CFC Press, NY 1984); Liposomes, Ortro (Marcel Schher, 1987); Methods Biochem Anal. 33:337462 (1988). Cationic lipids have been shown to mediate intracellular delivery of plasmid DNA (Feigner (1987) Proc. Natl. Acad. Sci. USA 84:7413–7416), and mRNA (Malone (1989) Proc. Natl. Acad. Sci. USA 86:6077–6081).

Determining Dosing Regimens

The pharmaceutical formulations of the invention can be administered in a variety of unit dosage forms, depending upon the particular condition or disease, the degree of chronic pain, the general medical condition of each patient, the method of administration, and the like. In one embodiment, the concentration of recombinant virus in the pharmaceutically acceptable excipient is between about $10^3$ to about $10^{18}$ or between about $10^5$ to about $10^{15}$ or between about $10^6$ to about $10^{13}$ particles per mL in an aqueous solution. The amount of recombinant virus administered can also be determined by titering and aliquoting "infectious units" (see, e.g., Xiao (1998) supra). Details on dosages are well described in the scientific and patent literature, see, e.g., the latest edition of Remington's Pharmaceutical Sciences, Maack Publishing Co, Easton Pa.; Sterman (1998) Hum. Gene Ther. 9:1083–1092; Smith (1997) Hum. Gene Ther. 8:943–954.

The exact amount and concentration of virus and the amount of formulation in a given dose, or the "therapeutically effective dose" is determined by the clinician, as discussed above. The dosage schedule, i.e., the "dosing regimen," will depend upon a variety of factors, including the amount of chronic pain present, the duration of the pain, the stage and severity of the disease or condition associated with the chronic pain (if any), and the general state of the patient's health, physical status, age and the like. The state of the art allows the clinician to determine the dosage regimen for each individual patient and, if appropriate, concurrent disease or condition treated. The illustrative example provided below can be used as guidance to determine the dosage regiment, i.e., dose schedule and dosage levels administered when practicing the methods of the invention.

Single or multiple intrathecal administrations of recombinant virus (e.g., AAV or adenoviral formulation can be administered, depending on the dosage and frequency as required and tolerated by the patient. Thus, one typical dosage for intrathecal administration is between about 0.5 to about 50 mL of a formulation with about $10^{13}$ viral particles per mL. In an alternative embodiment, dosages are from about 5 mL to about 20 mL are used of a formulation with about $10^9$ viral particles per mL. Lower dosages can be used, such as is between about 1 mL to about 5 mL of a formulation with about $10^6$ viral particles per mL. Based on objective and subjective criteria, as discussed herein, any dosage can be used as required and tolerated by the patient.

The exact concentration of virus, the amount of formulation, and the frequency of administration can be adjusted depending on the levels of recombinant beta-endorphin measured in the CSF after an initial administration. Means to sample CSF and quantitate levels of beta-endorphin are well known in the art, see, e.g., U.S. Pat. No. 4,096,237; Imasato (1997) Spinal Cord 35:757–762.

Routes of administration

The pharmaceutical compositions of the invention can be administered by any means known in the art, e.g., intrathecally, subdurally, or any means which delivers the composition approximate to the spinal chord parenchymal tissue. In a preferred embodiment, the pharmaceutical composition is administered intrathecally in a pharmaceutically acceptable excipient. Means to administer solutions into the subarachnoid space, i.e., intrathecally, into the CSF, are well known in the art; see, e.g., Oyama, T., U.S. Pat. No. 4,313,937.

After intrathecal (or other) injections, the recombinant virus (e.g., AAV or adenovirus) expression vector infects the pia mater connective tissue. Subsequently, recombinant beta-endorphin is secreted into (released approximate to) spinal cord parenchymal tissue (see, e.g., Iadarola, et al., "Gene Transfer Approaches to Pain Control," in Molecular Neurobiology of Pain, Progress in Pain Research and Management, Vol. 9, pg 337–359, ed. Borsook, D., IASP Press, Seattle, 1997).

However, a variety of means to administer endogenous opioid peptides can be used, including, e.g., implantation of cells which secret the recombinant virus (e.g., AAV or adenovirus) of the invention.

Kits

In one embodiment, the invention provides a kit for the treatment of chronic pain in a human which includes a pharmaceutical composition of the invention. In one embodiment, the kit contains instructional material teaching preferred indications, dosages and schedules of administration, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following example is offered to illustrate, but not to limit the claimed invention.

Example 1

Controlling Chronic Pain with Beta Endorphin

The following example details a study which demonstrates that the methods of the invention are an effective treatment for chronic pain while at the same time not affecting basal nociceptive responses. In particular, the following example details a study which demonstrates that intrathecal injection of recombinant adenovirus resulted in efficient infection of cells of the pia mater and secretion of recombinant beta-endorphin into the spinal cord parenchymal tissue. Sufficient recombinant beta-endorphin was secreted to ameliorate a symptom of chronic pain, specifically, hyperalgesia. Using the composition and method of the invention in an appropriate and art-recognized animal model, it was demonstrated that levels of in vivo generated beta-endorphin were sufficient to significantly desensitize the animals to the hyperalgesia induced by the chronic pain of inflammation. These studies demonstrate that the compositions and methods of the invention provide a novel gene therapy approach to treating chronic pain.

The animal model experiments described herein can be used by the skilled artisan to determine whether a pharmaceutical is within the scope of the invention, i.e., whether an adenoviral composition can selectively treat chronic pain while at the same time not significantly affecting the ability to perceive protective, acutely painful stimuli.

Construction of a Beta Endorphin Fusion Protein Coding Sequence

The goal was to construct a recombinant beta-endorphin fusion protein capable of being processed by connective tissue (pia mater) pro-peptide processing enzymes followed by secretion of a biologically active peptide. A coding sequence for a human beta-endorphin-mouse nerve growth factor (NGF) pre-pro-sequence fusion protein was constructed essentially as described by Beutler (1995) J. Neurochem. 64:475–481. Briefly, the beta-endorphin the 93 base pair long nucleic acid sequence encoding human beta-endorphin, a biologically active peptide in a 31 amino acid long form was synthesized de novo by standard in vitro chemical techniques. The resultant nucleic acid sequence coded for NGF-beta-endorphin fusion protein with the sequence YGGFMTSEKSQTPLVTLFKNAIIKNAYKKGE (SEQ ID NO:1) (representing the proteolytically processed gene product: human beta endorphin).

The 363 base pair long pre-pro-sequence of mouse nerve growth factor (NGF) was obtained by amplifying its 363 base pair length by polymerase chain reaction (PCR) using the amplification primers 5'-C CGA TAC GAA TTC GCC ACC ATG TCC ATG-3' (SEQ ID NO:2) and (reverse primer) 5'-TC GGA GGT CAT GAA ACC GCC ATA GCG CTT GCT-3' (SEQ ID NO:3). NGF coding sequence was fused in-frame upstream to the human beta-endorphin coding sequence to generate the fusion protein coding sequence. Thus, in the recombinant fusion protein, the pre-pre sequence is in the amino terminal half of the peptide. A Kozak translation-initiation sequence ACCATG (SEQ ID NO:6) was inserted 5' to the start codon to complete the nucleic acid sequence to be inserted into the expression vector. The fidelity of the sequence was confirmed by di-deoxy-nucleotide sequencing.

Construction of a Beta Endorphin Fusion Protein Expression Vector

The fusion protein coding sequence was subcloned into a recombinant adenovirus expression vector capable of transducing non-dividing cells in vivo. Specifically, the coding sequence was subcloned as an EcoRI-BamHI fragment into the same sites of the shuttle adenovirus vector pACCMV.pLpA (Becker (1994) Methods Cell Biol. 43(Pt A):161–189. In this construct the coding sequence insert is under the control of a constitutive cytomegalovirus (CMV) promoter. The insert sequence was confirmed by dideoxy sequencing using primers flanking the insert. The resulting shuttle vector was used for recombination into replication-deficient (E1-deleted) adenovirus type 5 in cultured HEK-293 cells, which packaged and secreted the recombinant virus (Becker (1994) supra). Concentrated, purified virus was assayed for particle number ($5 \times 10^{11}$/mL) by absorption spectroscopy, and for pfu ($4 \times 10^9$/mL) by infection of 293 cells. A schematic of the structure of the resulting viral vector, under control of the constitutive CMV promoter, is shown in FIG. 1.

Secretion of Fusion Protein by Infected Cultured Cells

Before injecting the fusion protein-expressing recombinant adenovirus vector (Ad-beta-EP) into animals, its ability to infect cultured cells and direct beta-endorphin secretion by the infected cells was verified. Bovine smooth muscle cells (cat. #AG08595A, Coriel Institute, Camden, N.J.) were grown to confluence ($3.8 \times 10^6$ cells per well) in II mm dishes, with changes of medium each day. Ad-beta-EP was added to wells at day 0 (0, 0.5, 1, 5 and $10 \times 10^6$ pfu/ml media). The media was sampled at days 3 and 7. Beta-endorphin radioimmunoassay (Guillemin (1977) Biochem. Biophys. Res. Commun. 77:361–366; Nichols Institute Diagnostics, San Juan Capistrano, Calif., cat. #40-6060) was performed in duplicate on the medium. The medium of cells transduced with Ad-beta-EP contained high levels of beta-endorphin at 3 and 7 days post-infection. The response was both time- and dose-dependent with maximal levels of 3.5 pmol/mL media per day at 7 days post infection and $10^7$ plaque-forming units (pfu) of virus/mL of culture media.

This amount of beta-endorphin fusion protein secretion, 0.04 pmol/hr/million cells, is comparable to retroviral expression of this same gene in cultured fibroblasts, 0.180 pmol/hr/million cells, as reported by Beutler (1995) supra.

Secretion of Beta-Endorphin Fusion Protein After In Vivo Gene Transfer

The ability of the virus to secrete beta-endorphin fusion protein after in vivo gene transfer was demonstrated using a rat animal model. The recombinant virus was introduced into the animal's intracerebroventricular (i.c.v.) space, infecting ependymal cells lining the cerebral ventricles (like pia mater cells, ependymal are non-dividing connective tissue cells lining nerve parenchymal tissue). The amount of beta-endorphin secreted into the cerebrospinal fluid (CSF) was subsequently measured. All animal experiments were performed in accordance with NIH Animal Care and Use Committee guidelines.

Aliquots containing from $2 \times 10^0$ to $2 \times 10^8$ pfu (in ten-fold increments; pfu assessed on 293 cells) were injected by stereotaxic placement of a needle into one lateral brain ventricle. These samples were formulated from a virus solution stock of $4 \times 10^9$ infectious particles/mL; $10^{11}$ viral particles/mL was diluted into 50 mM Tris pH 7.4, 10% glycerol, 10 mM $MgCl_2$.

Gene transfer into the ependymal cells was ascertained by i.c.v. coinjection of a recombinant adenovirus vector expressing beta-galactosidase, Ad-lacZ (Iadarola (1997) supra). Transduction of the ependymal cells in the ventricular system was judged by X-gal histochemistry of the lateral ventricles and immunofluorescence microscopy of the peri-aqueductal region for the lacZ gene product. X-gal histochemistry of the ventricle was used, as described by Bajocchi (1993) Nat. Genet. 3:229–234). Briefly, after perfusion with 4% para-formaldehyde, 2 mm slices of brains were reacted with X-gal. Anti-beta-galactosidase immunofluorescence of the peri-aqueductal region of rat brain was performed 3 days after injection of virus into one lateral ventricle. Sections of brain (30 um) processed through polyclonal rabbit anti-beta-galactosidase (5'-3', Boulder, Colo.) at 1:100,000, followed by biotinylated anti-rabbit secondary antibody, avidinbiotin complex (ABC, Vector Laboratories), and fluorescein tyramide (NEN Life Science) detection. Photographs of sections were digitally converted to black and white. Transduction of the ependymal cells throughout the ventricular system, demonstrated by intracellular expression of beta-galactosidase, was evident by 3 days after injection, as judged by both techniques.

Secretion of the recombinant, secreted beta-endorphin was then measured. CSF was readily sampled from the cisterna magna after adenoviral injection into the lateral ventricle. CSF was removed by insulin syringe placed in the cisterna magna, followed by boiling of the CSF in water and centrifugation (12,000×g, 5 min) and radioimmunoassay.

At one day post injection i.c.v., CSF was withdrawn and analyzed for secreted human beta-endorphin. The amount of secreted beta-endorphin increased with increasing amounts of virus injected, to a maximum of 0.3 pmol/mL at 200 million pfu injected. This was at least a ten-fold increase compared to normal CSF beta-endorphin levels found in rat (about 0.035 pmol/mL; Kiser (1983) Brain Res. 288:187–192) or human (about 0.015 pmol/mL; Nakao (1980) J. Clin. Endocrinol. Metab. 50:230–233). These results demonstrated that ependymal cells can cleave the mouse nerve growth factor pre-pro-sequence of the fusion protein and efficiently secrete the resultant recombinant human beta-endorphin in vivo.

The time course of secreted beta-endorphin production was analyzed. At three days after i.c.v. injection the level of beta-endorphin in the CSF peaked at about 0.6 pmol/mL. After fifteen days post injection, intrathecal levels of the beta-endorphin had returned to endogenous (0.03 pmol/mL) levels, i.e., recombinant human beta-endorphin was no longer detectable in the CSF.

In Vivo Expression of Beta-Endorphin Attenuates Thermal Hyperalgesia

To demonstrate that in vivo transduction and expression of beta-endorphin attenuates a symptom of chronic pain—hyperalgesia, a rat thermal hyperalgesia model was used. This method measures cutaneous hyperalgesia to thermal stimulation in unrestrained animals, and was performed essentially as described by Hargreaves (1988) Pain 32:77–88. Briefly, after administration of expression vector, baseline thermal hyperalgesia is assessed by paw withdrawal latency to thermal stimulus. Inflammation is then induced with unilateral injection of 6 mg carrageenan (type IV Sigma C-3889) in volume of 0.15 mL PBS into a hindpaw of a 200–300 g male rat. Paw withdrawal latency to thermal stimulus is again measured on both the inflamed and uninflamed paws.

In these studies, rats were injected intrathecally (i.t.) in the lumbar region of the spinal cord. Intrathecal (i.t.) administration of viral vector produces transgene expression spread over the surface of the spinal cord anatomically proximate the site of injection. The lumbar spinal cord was specifically chosen because it is innervated by primary afferents from the hind paw, the test site for the thermal hyperalgesia pain model.

The animals were injected either with control virus Ad-lacZ, or Ad-beta-EP. Catheter placement was 3 cm below the rostral end of the C1 vertebrae. 80 million pfu of Ad-beta-EP or Ad-lacZ in a volume of 10 microliters was administered. After 3 days post-surgery, paw withdrawal latency to thermal stimulus was performed to determine baseline thermal hyperalgesia. Data points were collected representing the mean and standard error of ipsilateral paw withdrawal latency of 33 uninflamed animals or approximately 17 test animals. Latencies were measured at different times post-inflammation.

Production of beta-endorphin and its secretion into the CSF was also assessed.

At 7 days post-injection, the CSF of animal injected with Ad-beta-EP had beta-endorphin levels ranging from 0.1 to 0.4 pmol/mL, compared to 0.03 pmol/mL for mock-injected animals.

The radiant thermal hyperalgesia test was performed at three days post-i.t. injection of vector. Injection of the vectors had no observable effect on basal nociception. Three days after virus injection, the (control) uninflamed paw withdrawal latencies were 8.7±−2.6 seconds ("sec") for Ad-lacZ, and 8.9±−2.5 sec for Ad-beta-EP (mean+standard error; N=33 for each virus).

In contrast, in the inflamed hindpaw, a marked decrease in withdrawal latency in the Ad-lacZ (no beta endorphin control) group was observed, an indication of hyperalgesia. Three hours after induction of inflammation, the latencies in the Ad-lacZ group were 2.3−±0.6 sec, N=17.

In contrast, this hyperalgesia was attenuated in the Ad-beta-EP test group to a withdrawal latency of 3.8±−1.9 sec, N=17. This is a significant reduction in hyperalgesia ($p<0.0004$, paired t test). If animals with beta-endorphin levels of less than 0.063 pmol/mL (the upper bound of the 95% confidence interval for the control group) were excluded from the analysis, the mean withdrawal latency increased from 3.8 sec to 4.5±−2.0 sec, N=8 (95% CI, 3.2 sec to 5.9 sec).

Neither the inflammation in the test paw nor any of the virus samples had any effect on nociceptive responsiveness in the uninflamed control paw. Since the control group had normal response to inflammatory hyperalgesia, the reduction (attenuation) of hyperalgesia was due to the Ad-beta-EP-generated, secreted beta-endorphin.

Since different levels of beta-endorphin would be expected to have different effects upon hyperalgesia (the more beta-endorphin, the greater the pain reduction), we examined beta-endorphin levels in the CSF of animals injected with Ad-beta-EP over a seven day time period. At 3 days post injection, inflamed latencies were obtained, and correlated with beta-endorphin levels observed in cisternal CSF after 7 days post injection. Beta-endorphin levels varied, but were higher than endogenous levels and showed a correlation with an increase in paw withdrawal latency (pain desensitization). This dose-response effect is further evidence that the attenuation of hyperalgesia was due to the Ad-beta-EP generated beta-endorphin.

Antagonism of Beta-Endorphin Chronic Pain Attenuation by Naloxone

Beta-endorphin's role in ameliorating chronic pain in the thermal hyperalgesia test was further demonstrated using the opioid antagonist naloxone. Naloxone is a competitive antagonist of opioid-specific effects, including opioid peptides, such as beta-endorphin. Thus, naloxone's ability to abrogate beta-endorphin's ameliorating effect on hyperalgesia is further evidence that the Ad-beta-EP-generated, secreted beta-endorphin is responsible for the reduction of hyperalgesia.

Naloxone has been shown to abrogate the analgesic effect induced by beta-endorphin; in rats where blockade of acute pain responses (tail pinch, hot plate, and electrical stimulation) by encapsulated cells secreting beta-endorphin was attenuated by naloxone (Saitoh (1995) J. Neurosurg. 82:630–634).

After about three to four hours of inflammation, naloxone at 2 mg/kg was injected intraperitoneally. Paw withdrawal latencies were examined at about 30 to 45 min post-injection to allow time for distribution of the naloxone. The withdrawal latencies of animals injected i.t. with Ad-lacZ before induction of inflammation were unaffected by naloxone treatment.

In contrast, after induction of inflammation, withdrawal latencies of the Ad-beta-EP group were significantly reduced by naloxone treatment ($p<0.04$, one-tailed t test) to a level indistinguishable from the Ad-lacZ group (i.e., the pain desensitization induced by Ad-beta-EP was blocked by naloxone). This also demonstrates that the attenuation of hyperalgesia by Ad-beta-EP was dependent upon an opioid-like mechanism.

The reduction in hyperalgesia (pain desensitization) observed with Ad-beta-EP in this pain model is 30–50% of that observed with morphine; i.e., paw withdrawal latencies increase half-way back to baseline levels with Ad-beta-EP, compared to all the way baseline with morphine (more pain desensitization) (Hargreaves (1988) supra). Several reasons for such a difference between morphine and beta-endorphin can be postulated. The rat thermal inflammation test used in these experiments is a more stringent test of hyperalgesia than that used by Hargreaves (1988) supra. Thus, the results described above may underestimate of true analgesic efficacy of recombinant beta-endorphin in this pain model.

Systemic morphine affects both the inflamed (chronic pain model) and uninflamed (basal nociceptive response) latencies, whereas Ad-beta-EP affects the inflamed latency selectively. These results demonstrate that the methods of the invention treat chronic pain without significantly affecting basal nociceptive responses.

The level of pain desensitization can be increased by increasing the beta-endorphin-expressing viral titer, the longevity or transcriptional rate of recombinant peptide expression, modifying the secretion signal, or stabilizing the beta-endorphin produced by the addition of peptidase inhibitors or use of sequence modifications of beta-endorphin (as described above), and the like.

As noted above, i.t. viral vector produces transgene expression spread over the surface of the spinal cord. Thus, the exact point of administration is less crucial than with intraparenchymal administration. This has a therapeutic implication for gene therapy for pain in that virus does not have to be injected precisely at the site of pain innervation.

Example 2

Controlling Chronic Pain with Beta Endorphin Expressed by Recombinant Adeno-Associated Virus (AAV) Expression Cassettes The following example details a second study which demonstrates that the methods of the invention are an effective treatment for chronic pain while at the same time not affecting basal nociceptive responses. In particular, the following example details a study which demonstrates that intrathecal injection of recombinant Adeno-Associated Virus (AAV) expression cassettes expressing beta endorphin resulted in efficient infection of cells of the pia mater and secretion of the recombinant beta-endorphin peptide into the spinal cord parenchymal tissue. Sufficient recombinant beta-endorphin was secreted to ameliorate a symptom of chronic pain, specifically, hyperalgesia. Using a second exemplary recombinant vector—AAV—with the method of the invention in an appropriate and art-recognized animal model it was again demonstrated that levels of in vivo generated beta-endorphin were sufficient to significantly desensitize the animals to the hyperalgesia induced by the chronic pain of inflammation. This study further demonstrates that the compositions and methods of the invention provide a novel gene therapy approach to treating chronic pain.

The animal model experiments described herein can be used by the skilled artisan to determine whether a pharmaceutical is within the scope of the invention, i.e., whether a recombinant virus, such as AAV or adenovirus, can selectively treat chronic pain while at the same time not significantly affecting the ability to perceive protective, acutely painful stimuli.

Construction of a Beta Endorphin Fusion Protein Coding Sequence

The goal was to construct a recombinant beta-endorphin fusion protein capable of being processed by connective tissue (pia mater) pro-peptide processing enzymes followed by secretion of a biologically active peptide. The same beta-endorphin construct (encoding a human beta-endorphin-mouse nerve growth factor (NGF) pre-pro-sequence fusion protein) used in the experiments described in Example 1, above, were incorporated into AAV expression cassette vectors. Thus, in the recombinant fusion protein, the pre-pre sequence is in the amino terminal half of the peptide.

The example shown also incorporates the di-cistronic aspect. Thus, the second transcript is preceeded by a Kozak translation-initiation sequence ACCATG (SEQ ID NO:6) inserted 5' to the start codon of the second transcript (eGFP) to complete the nucleic acid sequence to be inserted into the AAV expression vector.

Construction of a Beta Endorphin Fusion Protein Expression Vector

The fusion protein encoding construct was subcloned into a recombinant AAV expression vector capable of transducing non-dividing cells in vivo. The coding sequence was first subcloned into a shuttle vector as an EcoRI-BamHI fragment. In this construct the coding sequence insert is under the control of a constitutive cytomegalovirus (CMV) promoter. The insert sequence was confirmed by dideoxy sequencing using primers flanking the insert.

The resulting shuttle vector was used for recombination into replication-deficient AAV in cultured HEK-293 cells, which packaged and secreted recombinant AAV. Concentrated, purified virus was assayed for particle number by absorption spectroscopy, and for pfu by infection of 293 cells.

Secretion of Fusion Protein by Infected Cultured Cells

Before injecting the fusion protein-expressing recombinant AAV vector (AAV-beta-EP) into animals, its ability to infect cultured cells and direct beta-endorphin secretion by the infected cells was verified. Bovine smooth muscle cells (cat. #AG08595A, Coriel Institute, Camden, N.J.) were grown to confluence ($3.8 \times 10^6$ cells per well) in 11 mm dishes, with changes of medium each day. AAV-beta-EP was added at day 0 at 100 viral particles per cell (the -■- line), 1000 viral particles per cell (the -▲- line) and 10,000 viral particles per cell (the -♦- line); see FIG. 2.

Figure 2:
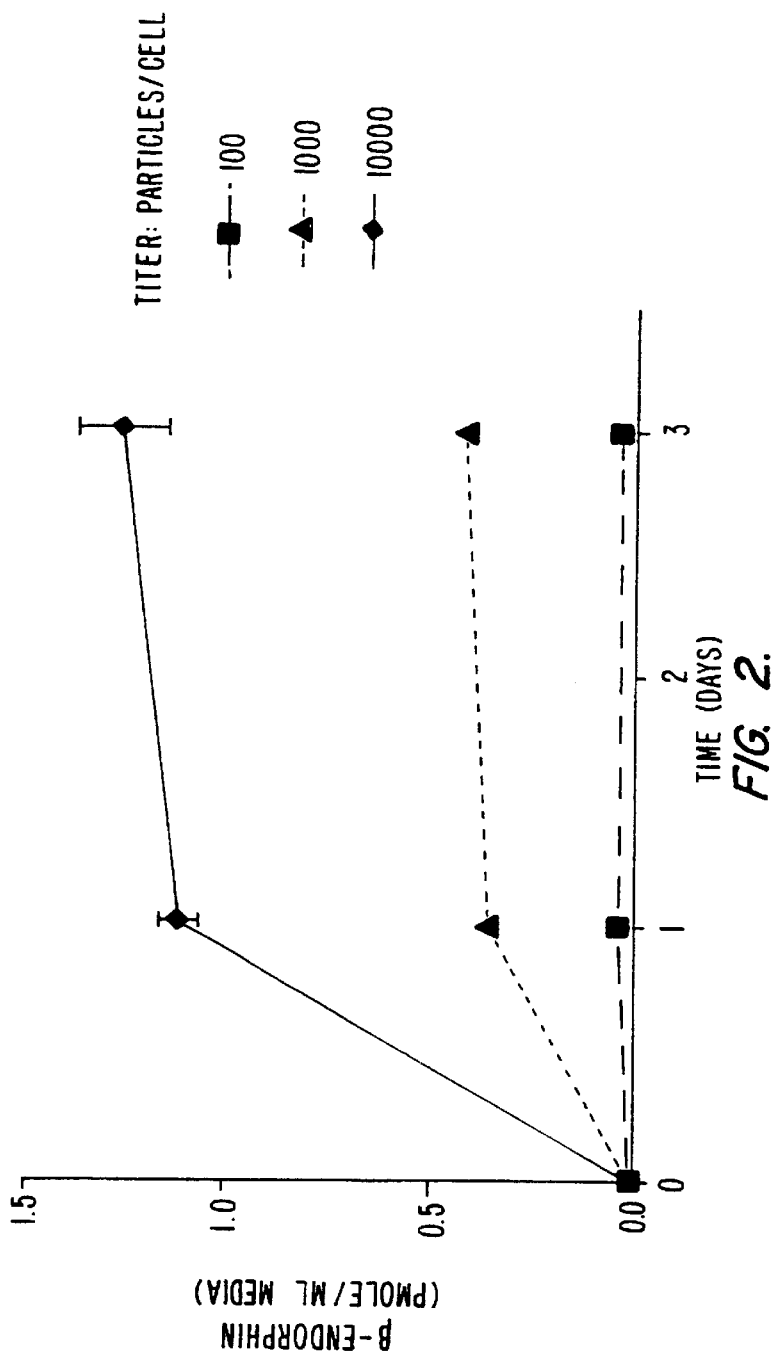
FIG. 2 summarizes the results of experiments demonstrating that beta-endorphin (SEQ ID NO:1) (the proteolytically processed gene product: human beta endorphin) is secreted from tissue culture cells infected in vitro with the AAV-beta endorphin expressing recombinant AAV vector, described in detail, below.

The media was sampled in triplicate at days 0, 1 and 3. Beta-endorphin radioimmunoassay (as in Guillemin (1977) Biochem. Biophys. Res. Commun. 77:361–366; with Nichols Institute Diagnostics, San Juan Capistrano, CA, cat. #40-6060) was performed in duplicate on the sampled medium. The amount of beta-endorphin secreted was both time and dose-dependent, as illustrated by FIG. 2. Maximal levels of secreted beta-endorphin, between about 1.1 and 1.2 (at day 1) and about 1.3 to 1.4 pmol/mL (at day 5) were measured in media samples from the 10,000 particles per cell well samples. Levels of secreted beta-endorphin from the 1,000 particles per.cell well samples were significantly lower, at between about 0.3 (at day 1) and about 0.4 pmol/mL (at day 5).

In Vivo Expression of Beta-Endorphin Attenuates Thermal Hyperalgesia

To demonstrate that in vivo transduction and expression of beta-endorphin using the AAV recombinant expression system can also attenuate hyperalgesia, the rat thermal hyperalgesia model was also used (as with Example 1, above). As noted above, this method measures cutaneous hyperalgesia to thermal stimulation in unrestrained animals. It also was performed essentially as described by Hargreaves (1988) supra.

In these studies, rats were injected intrathecally (i.t.) in the lumbar region of the spinal cord. Intrathecal (i.t.) administration of viral vector produces transgene expression spread over the surface of the spinal cord anatomically proximate the site of injection. The lumbar spinal cord was specifically chosen because it is innervated by primary afferents from the hind paw, the test site for the thermal hyperalgesia pain model.

The animals were injected with the AAV-beta-EP vector. Catheter placement was 3 cm below the rostral end of the CI vertebrae. $10^{11}$ particles of AAV-beta-EP in a volume of 10 microliters was administered. After 30 days post-surgery, paw withdrawal latency to thermal stimulus was performed to determine baseline thermal hyperalgesia. Data points were collected representing the mean and standard error of ipsilateral paw withdrawal latency of 5 uninflamed animals and 5 test animals (five animals per time point). Latencies were measured at different times post-inflammation.

Figure 3:
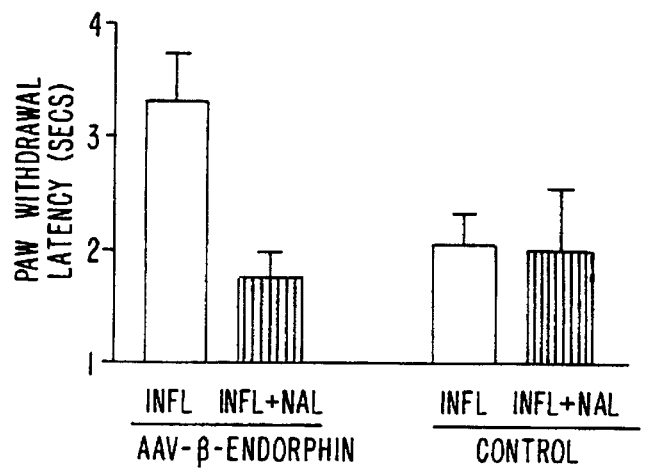
FIG. 3 summarizes the results of animal model experiments demonstrating that chronic pain can be treated in vivo by administration of AAV-beta endorphin expressing recombinant AAV vector, described in detail, below.

The radiant thermal hyperalgesia test was performed at 30 days post-i.t. injection of AAV vector and is summarized schematically in FIG. 3. At day 30, test paws were inflamed with carrageenan and tested at four hours. In the inflamed hindpaws, a marked increase in withdrawal latency in the AAV-beta endorphin group was observed, indicating reduction (attenuation) of hyperalgesia. Four hours after induction of inflammation, the latencies in the AAV-beta endorphin group increased from about two seconds to about just over 3 seconds. Paw withdrawal latency in the control group (animals injected i.t. with Ad-lacZ) was about 2 seconds.

Antagonism of Beta-Endorphin Chronic Pain Attenuation by Naloxone

Beta-endorphin's role in ameliorating chronic pain in the thermal hyperalgesia test was further demonstrated using the opioid antagonist naloxone. Naloxone is a competitive antagonist of opioid-specific effects, including opioid peptides, such as beta-endorphin. Thus, naloxone's ability to abrogate beta-endorphin's ameliorating effect on hyperalgesia is further evidence that the AAV-beta-EP-generated, secreted beta-endorphin is responsible for the reduction of hyperalgesia.

After about three to four hours of inflammation, naloxone at 1 mg/kg was injected intraperitoneally. Paw withdrawal latencies were examined at about 30 to 45 min post-injection to allow time for distribution of the naloxone.

As illustrated in Example 4, the withdrawal latencies of control animals injected i.t. with Ad-lacZ before induction of inflammation were unaffected by naloxone treatment. In contrast, after induction of inflammation, withdrawal latencies of the AAV-beta-EP group were significantly reduced by naloxone treatment to a level indistinguishable from the control Ad-lacZ group (i.e., the pain desensitization induced by AAV-beta-EP was blocked by naloxone). This also demonstrates that the attenuation of hyperalgesia by AAV-beta-EP was dependent upon an opioid-like mechanism.

As noted above, i.t. viral vector produces recombinant vector expression spread over the surface of the spinal cord. Thus, the exact point of administration is less crucial than with intraparenchymal administration. This has a therapeutic implication for gene therapy for pain in that virus does not have to be injected precisely at the site of pain innervation.

Example 3

Construction and Expression of a Bicistronic Message (Beta-Endorphin and a Second Polypeptide) by an IRES-Containing AAV Expression Cassette The following example details the construction of a recombinant AAV expression vector that expresses a bicistronic message comprising a beta-endorphin coding sequence. It also describes a novel IRES element.

In this example, a recombinant AAV vector is designed to express a bicistronic message, wherein the first cistron encodes pre-pro human beta-endorphin and the second cistron sequence encodes enhanced green fluorescent protein (EGFP). EGFP expression allows localization of cells that have received the recombinant virus and are expressing polypeptide in the transfected cell.

Development of a Novel IRES Motif

A novel IRES element was designed having the following sequence: 5'-GATCCACCGGTCGCCACC-3' (SEQ ID NO:4).

This IRES was inserted between cistron-1 (encoding pre-pro-beta-endorphin) and cistron-2 (encoding EGFP) of the bicistronic message sequence (the entire intercistronic sequence, as in FIG. 4A, is 5'-TAG GATCCACCGGTCGC-CACC ATG GTG-3' (SEQ ID NO:5). FIG. 4A also aligns, for sequence comparative purposes, a consensus Kozak sequence (motif) 5'-GCCGCCRCCATG-3' (SEQ ID NO:7) with a portion of SEQ ID NO:5. The eukaryotic consensus Kozak sequence in the message (transcript) is 5'-GCCGCCRCCAUGG-3' (SEQ ID NO:8). FIG. 4A shows the sequence of the IRES element (SEQ ID NO:4) and its relationship to other elements of the bicistronic message. FIG. 4B shows the expression cassette used in the bicistronic beta-endorphin- and EGFP-expressing AAV vector.

The full sequence of the nucleic acid encoding the bicistronic message is 5'-ATGTCCATGTTGTTCTACAC TCTGATCACTGCGTTTTTGATCGGCGTACAGG-CAGAACCGTACACAGATAGCAATGTCCAGAAGG-AGACTCTGTCCCTGAAGCCCACTGGACTAA-ACTTCAGCATTCCCTTGACACAGCCCTCCGC-AGAGCCCGCAGTGCCCCTACTGCACCAATAGCTG-CCCGAGTGACAGGGCAGACCCGCAACATCACTGT-AGACCCCAGACTGTTTAAGAAACGGAGAC-TCCACTCACCCCGTGTGCTGTTCAGCACCCAGCCT-CCACCCACCTCTTCAGACACTCTGGATCTAGA-CTTCCAGGCCCATGGTACAATCCC-TTTC-AACAGGACTCACCGGAGCAAGCGTTACG-GCGGTTTCATGACCTCCGAGAAGAGCCAGAC-GCCCTGGTGACGCTGTTCAAAAACGCCATCATCA-AGAACGCCTACAAGAAGGGCGAGTGA-3' (SEQ ID NO:9).

Assembly of the Dicistronic Translational Unit in the AAV Beta Endorphin Vector

Eco RI and Barn HI restriction enzymes were used to dissect the cDNA from the plasmid. Briefly, the beta-endorphin peptide coding region was fused to a cDNA fragment coding for the leader peptide of the neuronal growth factor(NGF) as described in Beutler (1995) 64:475–481. This chimera resulted in production of NGF-β-endorphin fusion protein which undergoes proteolytic cleavage to release nascent β-endorphin secreted in the supernatant. The Eco RI and Bam HI fragment were subcloned at the same restriction enzyme sites in the pEGFP-N1 preceding the EGFP coding region (Clontech), referred to as pENDO-N1. The production of beta-ENDO and EGFP was verified by transient expressions of the pENDO-N1 plasmid in Cos7 cells and determining the neuropeptide by radioimmunoassay from the supernatant and scanning the cell layer by fluorescence confocal microscopy.

Construction and Production of the AAV Vector

The dicistronic, beta endorphin-IRES18-EGFP translation cassette was removed from the pENDO-N1 plasmid vector with the Eco RI and Not I restriction enzymes and transferred into the pZAC AAV shuttle vector using the same restriction enzyme sites. Large scale preparation of pZAC-ENDO-N1 vector was carried out with the Qiagen endo-free kit for use in transient transfection studies employing Cos7 cells as hosts and to produce recombinant AAV. The production of beta-ENDO from the AAV vector was verified by transient expressions of the pENDO-N1 AAV in Cos7 cells and determining the neuropeptide by radioimmunoassay from the supernatant. Expression of EGFP from the AAV vector in Cos7 cells was confirmed by Western blot and scanning the cell layer by fluorescence confocal microscopy. Conventional procedures (including Western blots, radioimmunoassays, and the like) were used for all experiments.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating chronic pain by administering a beta-endorphin-expressing recombinant virus into a subarachnoid space, wherein basal nociceptive responses are not significantly affected, the method comprising the following steps:
   (a) providing a recombinant virus in a pharmaceutically acceptable excipient,
      wherein the recombinant virus is a recombinant adenovirus or a recombinant adeno-associated virus or a mixture thereof,
      wherein the recombinant virus comprises a nucleic acid insert encoding a beta-endorphin-secretion signal fusion protein,
      wherein the concentration of recombinant virus in the pharmaceutically acceptable excipient is between about $10^5$ to about $10^{15}$ particles per mL; and
   (b) administering the pharmaceutically acceptable excipient into the subarachnoid space or epidural space,
      wherein the recombinant virus infects the pia mater or arachnoid mater or dura mater connective tissue cells,
      wherein the infected cells express the fusion protein,
      wherein the fusion protein or a processed peptide is secreted into connective tissue interstitial space or cerebral spinal fluid or spinal chord parenchymal tissue in an amount effective to treat the chronic pain but not significantly affecting basal nociceptive responses.

2. The method of claim 1 wherein the concentration of recombinant virus in the pharmaceutically acceptable excipient is between about $10^6$ to about $10^{13}$ particles per mL.

3. The method of claim 1, wherein the nucleic acid insert encoding the beta-endorphin-secretion signal fusion protein is operably linked to a constitutively active promoter, wherein the fusion protein is constitutively expressed.

4. The method of claim 1, wherein the nucleic acid insert encoding the beta-endorphin-secretion signal fusion protein is operably linked to an inducible promoter.

5. The method of claim 4, further comprising the step of administering a composition capable of inducing the inducible promoter, wherein the fusion protein is expressed upon induction of the promoter.

6. The method of claim 1, wherein the secretion signal moiety of the fusion protein is a pre-pro sequence of human nerve growth factor (NGF).

7. The method of claim 1, wherein the pharmaceutically acceptable excipient is an aqueous solution.

8. The method of claim 1, wherein the recombinant virus further comprises a nucleic acid encoding a second polypeptide.

9. The method of claim 8, wherein the second polypeptide is selected from the group consisting of beta-endorphin-secretion signal fusion protein, human beta endorphin, an analog of beta-endorphin, enkephalin derived peptide, neurotensin, neuropeptide Y and green fluorescence protein.

10. The method of claim 8, wherein the nucleic acid encoding the second polypeptide is operatively linked to a promoter different from the promoter to which the beta-endorphin encoding nucleic acid is operatively linked.

11. The method of claim 8, wherein the nucleic acid encoding the second polypeptide is operatively linked to the same promoter the beta-endorphin encoding nucleic acid is operatively linked with and the two coding sequences are transcribed as a bicistronic message which is translated to produce both polypeptides.

12. The method of claim 11, wherein the bicistronic message comprises an IRES sequence.

13. The method of claim 12, wherein the IRES has a sequence as set forth in SEQ ID NO:4.

14. A pharmaceutical composition for treating chronic pain, comprising a recombinant virus in an excipient pharmaceutically acceptable for intrathecal administration, said recombinant virus defined as follows
   wherein the recombinant virus is a recombinant adenovirus or a recombinant adeno-associated virus or a mixture thereof,
   wherein the recombinant virus comprises a nucleic acid insert that is operably linked to an inducible promoter and encodes a beta-endorphin-secretion signal fusion protein comprising a human nerve growth factor (NGF) pre-pro sequence secretion signal moiety,
   wherein the recombinant virus concentration in the pharmaceutically acceptable excipient is between about $10^5$ to about $10^{15}$ particles per mL,
   wherein the recombinant virus can infect pia mater connective tissue cells subsequent to intrathecal administration, and
   wherein the recombinant virus, after infecting the pia mater connective tissue cells, expresses the fusion protein in the infected cell upon induction of the inducible promoter, and the infected cell secretes the fusion protein or a processed peptide into spinal chord parenchymal tissue.

15. The pharmaceutical composition of claim 14 wherein the concentration of recombinant virus in the pharmaceutically acceptable excipient is between about $10^6$ to about $10^{13}$ particles per mL.

16. The pharmaceutical composition of claim 14, wherein the pharmaceutically acceptable excipient is an aqueous solution or a lipid based solution.

17. A pharmaceutical composition for treating chronic pain, comprising a recombinant virus in an excipient pharmaceutically acceptable for intrathecal administration, said recombinant virus defined as follows
   wherein the recombinant virus is a recombinant adenovirus or a recombinant adeno-associated virus or a mixture thereof,
   wherein the recombinant virus comprises: (i) a nucleic acid insert encoding a beta-endorphin-secretion signal fusion protein comprising a human nerve growth factor (NGF) pre-pro sequence secretion signal moiety, and (ii) a nucleic acid insert encoding a second polypeptide that is operatively linked to the same promoter to which the beta-endorphin encoding nucleic acid is operatively linked and the two coding sequences are transcribed as a bicistronic message that comprises an IRES sequence as set forth in SEQ ID NO:4;
   wherein the recombinant virus concentration in the pharmaceutically acceptable excipient is between about $10^5$ to about $10^{15}$ particles per mL,
   wherein the recombinant virus can infect pia mater connective tissue cells subsequent to intrathecal administration,
   wherein the recombinant virus, after infecting the pia mater connective tissue cells, expresses the fusion protein in the infected cell and the infected cell secretes the fusion protein or a processed peptide into spinal chord parenchymal tissue.

18. The pharmaceutical composition of claim 17, wherein the second polypeptide is selected from the group consisting of beta-endorphin-secretion signal fusion protein, human beta endorphin, an analog of beta-endorphin, enkephalin derived peptide, neurotensin, neuropeptide Y, and green fluorescence protein.

19. The pharmaceutical composition of claim 17, wherein the concentration of recombinant virus in the pharmaceutically acceptable excipient is between about $10^6$ to about $10^{13}$ particles per mL.

20. The pharmaceutical composition of claim 17, wherein the pharmaceutically acceptable excipient is an aqueous solution or a lipid based solution.

* * * * *

```
                         SEQUENCE LISTING

<160> NUMBER OF SEQ ID NOS: 10

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence:nerve growth
      factor-beta (NGF-beta)-endorphin fusion protein

<400> SEQUENCE: 1

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr Lys Lys Gly Glu
             20                  25                  30

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 2
ccgatacgaa ttcgccacca tgtccatg                                       28

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:PCR
      amplification reverse primer

<400> SEQUENCE: 3
tcggaggtca tgaaaccgcc atagcgcttg ct                                  32

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:novel
      internal ribosome entry signal (IRES) element

<400> SEQUENCE: 4
gatccaccgg tcgccacc                                                  18

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:entire
      intercistronic sequence

<400> SEQUENCE: 5
taggatccac cggtcgccac catggtg                                        27
```

```
<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence:Kozak
      translation-initiation sequence

<400> SEQUENCE: 6 accatg                                                                        6

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:eukaryotic
      consensus Kozak sequence motif

<400> SEQUENCE: 7
gccgccrcca tg                                                                12

<210> SEQ ID NO 8
<211> LENGTH: 13
<212> TYPE: RNA
<213> ORGANISM: Artificial Sequence
<220> FEATURE:
<223> OTHER INFORMATION: Description of Artificial Sequence:eukaryotic
      consensus Kozak sequence in the message
      (transcript)

<400> SEQUENCE: 8
gccgccrcca ugg                                                               13

<210> SEQ ID NO 9
<211> LENGTH: 459
<212> TYPE: DNA
<213> ORGANISM: Artificial Sequence
<220> FEATURE:
<223> OTHER INFORMATION: Description of Artificial Sequence:full
      sequence encoding the bicistronic message

<400> SEQUENCE: 9
atgtccatgt tgttctacac tctgatcact gcgttttga tcggcgtaca ggcagaaccg       60
tacacagata gcaatgtccc agaaggagac tctgtccctg aagcccactg gactaaactt      120
cagcattccc ttgacacagc cctccgcaga gcccgcagtg cccctactgc accaatagct      180
gcccgagtga caggcagac ccgcaacatc actgtagacc ccagactgtt taagaaacgg       240
agactccact caccccgtgt gctgttcagc acccagcctc cacccacctc ttcagacact      300
ctggatctag acttccaggc ccatggtaca atcccttttca acaggactca ccggagcaag     360
cgttacggcg gtttcatgac ctccgagaag agccagacgc ccctggtgac gctgttcaaa      420
aacgccatca tcaagaacgc ctacaagaag ggcgagtga                            459

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence:Kozak
      consensus sequence

<400> SEQUENCE: 10
gccgccrcca tgg                                                               13
```